United States Patent [19]

Hogan, Jr.

[11] Patent Number: 5,962,412
[45] Date of Patent: Oct. 5, 1999

[54] METHOD OF MAKING POLYMERS HAVING SPECIFIC PROPERTIES

[75] Inventor: Joseph C. Hogan, Jr., Belmont, Mass.

[73] Assignee: Arqule, Inc., Medford, Mass.

[21] Appl. No.: 08/931,771

[22] Filed: Sep. 16, 1997

Related U.S. Application Data

[63] Continuation of application No. 08/290,720, Jun. 10, 1996, Pat. No. 5,670,480.

[51] Int. Cl.$^6$ .................................................. A61K 37/00
[52] U.S. Cl. ............................ 514/12; 528/310; 528/315; 528/322; 528/332; 528/422; 528/423; 528/425; 526/258; 530/323; 530/324; 530/333; 548/258
[58] Field of Search ............................... 514/12; 528/310, 528/315, 322, 332, 422, 423, 425; 526/258; 548/215; 530/323, 324, 333

[56] References Cited

U.S. PATENT DOCUMENTS

| | | | |
|---|---|---|---|
| 3,410,880 | 11/1968 | Brockenhurst | 360/404.9 |
| 3,450,673 | 6/1969 | McKillip | 260/75 |
| 3,485,806 | 12/1969 | Bloomquist et al. | 260/80.3 |
| 3,488,327 | 1/1970 | Kollinsky et al. | 260/78.3 |
| 3,488,389 | 1/1970 | McKillip | 260/561 |
| 3,499,032 | 3/1970 | Clemens et al. | 260/561 |
| 3,511,894 | 5/1970 | Markert | 260/875 |
| 3,527,802 | 9/1970 | Slagel | 260/561 |
| 3,555,095 | 1/1971 | Slagel | 260/584 |
| 3,565,868 | 2/1971 | Sedor et al. | 260/78.3 |
| 3,567,725 | 3/1971 | Grabowski et al. | 260/250 |
| 3,583,950 | 6/1971 | Kollinsky et al. | 260/78 |
| 3,598,790 | 8/1971 | Kollinsky et al. | 260/78.3 |
| 3,641,145 | 2/1972 | Culbertson | 260/558 |
| 3,664,990 | 5/1972 | Slagel | 260/85.5 |
| 3,671,473 | 6/1972 | Sedor et al. | 260/18 |
| 3,676,453 | 7/1972 | Pines et al. | 260/307 |
| 3,704,128 | 11/1972 | Koda et al. | 96/50 |
| 3,706,797 | 12/1972 | McKillip et al. | 260/558 |
| 3,706,800 | 12/1972 | Hartlage et al. | 260/561 |
| 3,715,343 | 2/1973 | Slagel et al. | 260/88.1 |
| 3,728,387 | 4/1973 | Freis et al. | 260/561 |
| 3,756,994 | 9/1973 | Culbertson | 260/82.1 |
| 3,781,319 | 12/1973 | Wawzonek et al. | 260/453 |
| 3,794,495 | 2/1974 | Ishihara et al. | 96/87 |
| 3,803,220 | 4/1974 | Gasman | 260/518 |
| 3,811,887 | 5/1974 | Ishihara et al. | 96/50 |
| 3,818,065 | 6/1974 | Schoellkopf et al. | 260/464 |
| 3,828,007 | 8/1974 | Throckmorton | 260/75 |
| 3,850,969 | 11/1974 | Grimm et al. | 260/404.5 |
| 3,893,974 | 7/1975 | Niino et al. | 260/47 |
| 3,898,087 | 8/1975 | Brutchen et al. | 96/33 |
| 3,904,749 | 9/1975 | McKillip | 424/71 |
| 3,925,284 | 12/1975 | Carleton et al. | 260/2.5 |
| 3,934,029 | 1/1976 | Kabara | 424/320 |
| 3,934,031 | 1/1976 | Kabara | 424/320 |
| 3,934,035 | 1/1976 | Kabara | 424/320 |
| 3,946,131 | 3/1976 | Biefeld et al. | 428/378 |
| 3,948,866 | 4/1976 | Pennewiss et al. | 260/79.3 |
| 3,963,703 | 6/1976 | Culbertson | 260/239 |
| 3,963,776 | 6/1976 | Middleton | 260/561 |

(List continued on next page.)

FOREIGN PATENT DOCUMENTS

| | | |
|---|---|---|
| 0 185 493 | 6/1986 | European Pat. Off. . |
| 0 212 617 | 4/1987 | European Pat. Off. . |
| 63 17933 | 4/1988 | Japan . |
| 1 181 218 | 2/1970 | United Kingdom . |
| 1 265 163 | 3/1972 | United Kingdom . |
| 93/20935 | 10/1993 | WIPO . |

OTHER PUBLICATIONS

Abstract. XP–002063092. Toko, Akira et al. "Photosensitive Resin Compositions".

Iwakura, Yoshio et al., "Synthesis of Polyamideamines from 5–Oxazolones". Journal of Polymer Science Part A–1, vol. 6, 785–791, 1968.

Markert, Gerhard et al., "Inhomogeneous Polymer Networks through Incompatibility". XP–002063091, p433.

Markert, Gerhard et al., "Inhomogene Netzwerke durch Unverträglichkeit". XP–002063090. pp. 199–212.

Tetrahedron Letters, 27, 6319 (1986).

Kardiologisisa, "Bioelectrical Mechanism", vol. 31, No. 7, 1991, pp. 52–55.

Kardiologisisa, vol. 30, No. 8, 1990, pp. 69–72.

J. Hetegel Chem., 1972, 9, 687–690, "Aminimides IX(1). A general Synthesis of 1–Substituted–2–imidazolidinones(2)", by David Aelony et al.

J. Org. Chem., vol. 41, No. 4, 1976, 715–716, "Acyl Migration in 2–Hydroxylalkyl Aminimides", by Meir Asscher.

Biopolymers, vol. 17, 1693–1711 (1978), "Experimental Conformational Study of Two Peptides Containing a–Aminoisobutyric Acid. Crystal Structure of N–Acetyl–a–Aminoisobutyric Acid Methylamide" by A. Aubry et al.

Tetrahedron Letters No. 31, pp. 2691–2694, 1976, "Pyridines as Leaving Groups in Synthetic Transformations: Nucleophilic Displacements of Amino Groups, and Novel Preparations of Nitriles and Isocyanates", by J.B. Bapat et al.

University College, Hull, Sep. 27, 1952, pp. 453–456, "The Dehydration and Racemisation of N–Acyl–L–aspartic Acids by Acetic Anhydride", by C.C. Barker.

(List continued on next page.)

*Primary Examiner*—Duc Truong
*Attorney, Agent, or Firm*—Pennie & Edmonds LLP

[57] ABSTRACT

A method of making a polymer having specific physiochemical properties by forming a first module having a structure which includes at least two structural diversity elements suitable to impart a desired physical property to a polymer which is made from said monomer; and reacting one or more modules to form a polymer having specific physiochemical properties. The base module can be formed by reacting a first compound having at least one structural diversity element and a first reactive group, with a second compound having at least one structural diversity element and a second reactive group, wherein the first and second groups combine by an addition reaction. Specifically, an aminimide compound, an oxazolone compound or derivatives thereof are useful as base modules in the invention.

24 Claims, No Drawings

5,962,412
Page 2

U.S. PATENT DOCUMENTS

| | | | |
|---|---|---|---|
| 3,968,065 | 7/1976 | Morris et al. | 260/23.5 |
| 3,969,298 | 7/1976 | Gasman | 260/29.6 |
| 3,983,166 | 9/1976 | Samour | 260/481 R |
| 3,985,807 | 10/1976 | Grimm et al. | 260/561 |
| 4,005,055 | 1/1977 | Miron et al. | 260/47 |
| 4,016,340 | 4/1977 | Kolesinski et al. | 526/7 |
| 4,022,623 | 5/1977 | Fitzgerald et al. | 96/114 |
| 4,046,658 | 9/1977 | Brown | 204/181 |
| 4,067,830 | 1/1978 | Kresta | 260/2.5 |
| 4,070,348 | 1/1978 | Kriemer et al. | 260/79.3 |
| 4,078,901 | 3/1978 | Sung et al. | 44/64 |
| 4,080,206 | 3/1978 | Kolesinski et al. | 96/29 |
| 4,097,444 | 6/1978 | Teige et al. | 260/40 |
| 4,102,916 | 7/1978 | Falk | 260/501.12 |
| 4,122,159 | 10/1978 | Madrange et al. | 424/45 |
| 4,140,680 | 2/1979 | Sullivan | 526/287 |
| 4,162,355 | 7/1979 | Tsibris | 526/293 |
| 4,189,481 | 2/1980 | Kabara | 424/248.54 |
| 4,212,905 | 7/1980 | Talbris | 427/221 |
| 4,213,860 | 7/1980 | Tsibris | 210/31 |
| 4,217,364 | 8/1980 | Kabara | 424/320 |
| 4,260,705 | 4/1981 | Tsibris | 525/330 |
| 4,280,008 | 7/1981 | Schoellkopf et al. | 548/301 |
| 4,304,705 | 12/1981 | Heilmann et al. | 260/30.4 |
| 4,378,411 | 3/1983 | Heilmann et al. | 428/500 |
| 4,424,272 | 1/1984 | Taylor | 430/507 |
| 4,451,619 | 5/1984 | Heilmann et al. | 525/379 |
| 4,485,236 | 11/1984 | Rasmussen et al. | 544/69 |
| 4,548,981 | 10/1985 | Kolesinski et al. | 524/555 |
| 4,563,467 | 1/1986 | Soler | 514/336 |
| 4,617,253 | 10/1986 | Taylor et al. | 430/323 |
| 4,624,995 | 11/1986 | Katritzky et al. | 525/452 |
| 4,645,711 | 2/1987 | Winslow | 428/355 |
| 4,667,012 | 5/1987 | Rasmussen et al. | 528/332 |
| 4,670,528 | 6/1987 | Taylor et al. | 526/263 |
| 4,695,608 | 9/1987 | Engler et al. | 525/308 |
| 4,705,824 | 11/1987 | Lin | 524/612 |
| 4,737,560 | 4/1988 | Heilmann et al. | 526/304 |
| 4,740,568 | 4/1988 | Katritzky et al. | 525/452 |
| 4,777,217 | 10/1988 | Rasmussen et al. | 525/279 |
| 4,777,276 | 10/1988 | Rasmussen et al. | 556/419 |
| 4,785,070 | 11/1988 | Rasmussen et al. | 528/73 |
| 4,816,554 | 3/1989 | Katritksy et al. | 528/210 |
| 4,841,021 | 6/1989 | Katritzky et al. | 528/407 |
| 4,852,969 | 8/1989 | Babirad et al. | 350/96.34 |
| 4,871,824 | 10/1989 | Heilmann et al. | 526/304 |
| 4,874,822 | 10/1989 | Rasmussen et al. | 525/279 |
| 4,898,923 | 2/1990 | Katritzky et al. | 528/73 |
| 4,948,715 | 8/1990 | Hulme-Lowe et al. | 430/495 |
| 4,981,933 | 1/1991 | Fazio et al. | 526/260 |
| 5,013,795 | 5/1991 | Coleman et al. | 525/279 |
| 5,039,813 | 8/1991 | Fazio et al. | 548/228 |
| 5,066,559 | 11/1991 | Elmasry et al. | 430/111 |
| 5,075,352 | 12/1991 | Elmasry | 523/201 |
| 5,081,197 | 1/1992 | Heilmann et al. | 526/260 |
| 5,091,489 | 2/1992 | Heilmann et al. | 526/90 |
| 5,094,766 | 3/1992 | Kepuscinski et al. | 252/51.5 |
| 5,138,071 | 8/1992 | Schoellkopf et al. | 548/537 |
| 5,147,957 | 9/1992 | Kumar | 528/15 |
| 5,149,806 | 9/1992 | Moren et al. | 544/72 |
| 5,157,108 | 10/1992 | Krepski et al. | 528/503 |
| 5,157,145 | 10/1992 | Schoellkopf et al. | 560/41 |
| 5,175,081 | 12/1992 | Krepski et al. | 430/617 |
| 5,185,102 | 2/1993 | Harelstad et al. | 252/582 |
| 5,194,623 | 3/1993 | Krepski et al. | 548/261 |
| 5,200,471 | 4/1993 | Coleman et al. | 525/326.9 |

OTHER PUBLICATIONS

Acta Chem. Scand. B 33 (1979) No. 2, "Electron Deficient Heteroar matic Ammonioamidates. XVII. N–(3–Quinazolinio)amindates. VI. The Photochemistry of N–(30Quinazolinio)amidates in the Presence of α–Toluenethiol", by G. Barta–Szalai et al.

J. Chem. Socl. Perkin Trans. I 1983, "Electron Deficient Heteroaromatic Ammonioamides. Part 24.[1]. N–(Quinazolin–3–io)amindates. Part 11.[2] The Photochemistry of N–(6,7–Methylenedioxyquinazolin–3–io)amidates in Acetone", by Gizella Barta–Szalai et al.

J. Heterocyclic Chem., 23, 375, 1986, "Novel Synthesis of Pyrido[2,1–fl]–as–Triazinium System and its Zwitterionic Derivatives . . . ", by S. Batori.

J. Heterocyclic Chem., 25, 437 (1988), "Regioselectivity in Methylation and Phenylation of the Zwitterionic Pyrido[2,1–f]–as–triazinium–1– and 3–olates and thiolates[1]", by Sandor Batori et al.

J. Heterocyclic Chem., 27, 1673 (1990), "Synthesis and Regiospecificity in Methylation of Pyrido[1,2–a]pyrazinium–1– and 3–olates and Pyrido[1,2–b]pyridazinium–2– and 4–olates [1]", by S. Batori et al.

J.C.S. Perkin II, 1978, 1173, "The Basicities of Substituted N–Trimethylammoniophenylacetamidates and N–Trimethylammoniocinnamamidates. The Hammett Correlations and the Thermodynamics of Protonation", by William H. Beck.

J.C.S. Perkin II, 1976, "The Basicities of N–Trimethylammonioacetamidate and of Substituted N–Trimethylammoniobenzamidates. The Hammett Correlation and the Thermodynamics of Protonation", by Wiliam H. Beck et al.

Tetrahedron Letters, No. 4, pp. 289–292, 1972, "The Curtius Rearrangement in Aminimides" by Herman P. Benecke et al.

J. Am. Chem. soc., 1982, 104, 2437–2444, "Solid–State and Solution Conformation of Homo Oligo–α–aminoisobutyric acids) from Tripeptide to Pentapeptide: Evidence for a 310 Helix[1a]", by Ettore Benedetti.

J. Am. Chem. Soc. 1984, 106, 8146–8152, Folded and Extended Structures of Homooligopeptides from α,α–Dialkylated Glycines. A Conformational Energy Computation and X–ray Diffraction Study, Ettore Benedetti et al.

"First Crystal Structure Analysis Of A Complete Homo–Oligopeptide Series", by Ettore Benedetti et al., pp. 619–624.

Gaza Chem. Ital. 95, 1965, "Reazione dei diarildiazoalcani–Nota IV. Difenildiazometano e azoici carbonilici", Gian Franco Bettinetti et al.

Nucleosides & Nucleotides, 10(8), 1657–1665, 1991 "Synthesis of N–Aminopyrazinium Analogs of Cytidine and 2'–Deoxycytidine", by Miroslav Bobek et al.

J. Am. Chem. Soc. 1984, 106, 8152–8156, "Folded and Extended Structures of Homooligopeptides from α,α–Dialkylated α–Amino Acids. An Infrared Absorption and H Nuclear Magnetic Resonance Study", by Gian Maria Bonora.

Bull. Soc. Chim. Belg., vol. 84/n4/1975, pp. 299–304, "Synthesis of a Homologous Series of Protected Oligopeptides Derived From L–Norvaline" by G.M. Bonora et al.

Tetrahedron vol. 38, No. 24, pp. 3579–3583, 1982, "(–)–Isovaline: Confirmation of its D–(=R)–Configuration by X–Ray Analysis of Its N–Chloroacetyl Derivative", by R. Bosch et al.

Tetrahedron Letters No. 31, pp. 2689–2690, 1976, "Allylic and Benzylic Deamination By Thermal Cleavage of 1–substituted 1,2–Dihydro–2, 4, 6–Triphenylpyridines" by A.J. Boulton et al.

Current Chemotherapy, vol. II, 1213–1216, "Observations on the Antineoplastic Activity of Aminimides", by L. Boutis et al.

Chemistry and Industry, Jul. 11, 1970, "Kinetics of reaction between gaseous oxygen and cobalt(II) ammines" by R. Bratchley et al.

Tetrahedron Letters vol. 21, 5059–5060, 1980, "New Cyclic Aminimides Containing Pyrazolone Skeleton", By M. Poje and N. Bregant.

Journal of Chemical and Engineering Data, vol. 12, No. 4, "Preparation of Some New Aminimides", by Melancthon S. Brown.

Biopolymers, vol. 12, 2599–2605 (1973), "An Obligatory a–Helical Amino Acid Residue" by Antony W. Burgess et al.

J. Chem Soc., 1972, 1071–1076, "Structural Investigations of Ylides. Part I. Crystal and Molecular Structures of Trimethylammoniobenzamidate and Trimethylammonionitramidate: Two Stabilised Nitrogen–Nitrogen Ylides", by A.F. Cameron.

Chemical Communications, No. 14, Jul. 21, 1971, 725–726, "Crystal and Molecular Structures of Two N–Ammonio-amidates", by A.F. Cameron.

Journal of Pharmaceutical Sciences, vol. 75, No. 4, Apr. 1986, 407–409, "2,2'–Phthaloyl–, 2,2'–Isophthaloyl–, and 2,2'–Terephthaloylbis[1,1,1–trimethylhydrazinium] Dihydroxie, Bis(Inner Salts): Synthesis, Partition Coefficients, Toxicity and Effect on Ganglionic Transmission", by Lindley A. Cates.

Chemical Abstracts, vol. 89, 1978, p. 250, Mosquito larvicidal and pupicidal activity of aminimides, by E. Clarke et al.

"Synthesis of 2,2'–Bis–[5(4H)–oxazolones]" by Charles S. Cleaver et al, 1954, vol. 77, pp. 1544–1546.

Meth and Find Exptl Clin Pharmacol 1987; 9(2):101–110, "Pharmacological Properties of Besulpamide, a New Diuretic, in Rats and Dogs", by M. Colombo, et al.

Biochemical and Biophysical Research Communications, vol. 79, No. 1, 1977, The Crystal and Molecular Structure of the Amino Terminal Tetrapeptide of Alamethicin. A Novel $3_{10}$ Helical Conformation.

Newcastle Technical Centre, 1274–1280, Jun. 1969, "Light Scattering by Polydisperse Cylindrical Micelles", by J.M. Corkill et al.

Tetrahedron, vol. 49, No. 15, pp. 3185–3192, 1993, "2–Alkoxycarbonylcycloimmonium Ylides, Efficient 1,4–Dipole Equivalents in the Synthesis of New Conjugated Betaines", by Ana M. Cuadro et al.

Journal of Polymer Science, Part A–1, vol. 6, 363–373 (1968), "Aminimides. IV. Homo– and Copolymerization Studies on Trimethylamine Methacrylimide", by B.M. Culbertson.

Macromolecules, vol. 1, p. 254, May–Jun. 1968, "Aminimides. VII. Homo– and Copolymerization Studies on 1,1–Dimethyl–1–(2–hyroxypropyl)amine–Methacrylimide . . . ", by B.M. Culbertson.

Aminimides, vol. 3, No. 6, Nov.–Dec. 1970, 715–722, "Aminimides. VIII Synthesis and Homo–and Copolymerization Studies of 1,11–Trimethylactrylylhydrazinium Chloride and 1,1,1–Trimethylmethacrylylhydrazinium Chloride", by B.M. Culbertson et al.

Journal of Polymer Science: Part A–1, vol. 6, 2197–2207 (1968), "Aminimides V. Preparation and Polymerization Studies of Trimethylamine–4–Vinylbenzimide", by B.M. Culbertson et al.

Applied Polymer Symposium No. 26, 399–410 1975, "Synthesis and Polymerization Studies of Aminimide Monomers Containing Acetoxyl or Carboxylic Acid Residues", by B.M. Culbertson et al.

J. Org. Chem, USSR 1966, 2, Aminimides cyclic.

Proceedings of the Seventh American Peptide Symposium, Peptides– Synthesis–Structure–Function, pp. 303–306, "Sterically–Hindered Amino Acids. Directors of Peptide Conformation", by N.G. Delaney et al.

Meth and Find Exptl Clin Pharmacol 1987; 9(2):111–119, "Acute, Subacute and Subchronic Toxicity of Besulpamide", by I. Demestre et al.

Tetrahedron vol. 48, No. 23, pp. 4733–4748, 1992, "Asymmetric Synthesis Of Unusual Amino Acids: An Efficient Synthesis of Optically Pure Isomers of β–Methylphenylalanine" by Ramalinga Dharanipragada et al.

Inorg. Nucl. Chem. Letters, vol. 10, pp. 233–235, 1974, "Ortho–Metallation Reactons With 1–Benzoyliminopyridinium Betaine", by Shelton A. Dias et al.

J. Chem Soc., 162, 1975, J.C.S. Dalton, "Metal–Ylide Complexes. Part I. Metallation Reactions . . . ", by Shelton A. Dias et al.

Chemical Abstracts, vol. 70, 1969, 264, "Synthesis of 1–alkyl–1,1–dimethylhydrazinium salts and N–alkyldimethylaminoacetimides and their properties", Kameyama, Eiichi et al.

Meth and Find Exptl Clin Pharmacol 1987; 9(2):121–126, "Pharmacokinetics of Besulpamide in Rats and Dogs", by J. Esteve.

Chemical Abstracts, vol. 115, 1991, p. 44, "Elimination of disturbances of the heart electric stability and arrhythmias with a synthetic analog of acetylcholine" by F.Meerson et al.

Polymer Bulletin 22, 449–454(1989), "Synthesis and reactivity of highly versatile VDMO–VBC copolymers" by Robert C. Fazio et al.

Tetrahedron, vol. 31, pp. 2559–2569, 1975, "N–(6, 7–Methylenedioxy–3–Quinazolinio)Amidates–I Synthesis Spectra and Some Dark Reactions", J. Fetter.

FEBS Letters, vol. 155, No. 2, "The crystal structure of a 310 helical decapeptide containing α–aminoisobutyric acid" by A.K. Francis.

J. Chem. Soc. Perkin Trans. II 1982, pp. 1235–1239, "The Crystal Structure of the Amino–terminal Pentapeptide of Suzukacillin. Occurrence of a Four–fold Peptide Helix", by Athappilly K. Francis.

Biopolymers, vol. 22, 1499–1505 (1983), "Crystal Structure of Boc–Ala–Aib–Ala–Aib–Aib–Methyl Ester, A Pentapeptide Fragment of the channel–Forming Inonophore Suzukacillin", by A.K. Francis et al.

J. Chem. Research (S), 192–193, 1988, "Photochemistry of Trialkylammonio–N–benzoylimides: Rearrangement and Amide Formation" by Sally Freeman et al.

J. Chem. Research(S), 354–355 1989, "Base–induced Rearrangement of 1,1,1,2–Tetraethyl–2–benzoylhydrazinium Iodide to N–(Dimethylaminomethyl)–N–methylbenzamide" by Sally Freeman et al.

Journal of the American Oil Chemists' Society, vol. 49, "Aminimides XIII Long Chain Aminimides and Isocyanates", by R.E. Freis et al.

J. Heterocyclic Chem., 26, (Sep.–Oct. 1989), 1373–1382, Study of the Structure of Besulpamide, 1–[–Chloro–3–sulfamoylbenzoyl)amino]2,4,6–trimethylpyridinium hydroxide inner salt, and related compounds, using X–ray Crystallography and 'H and $^{13}C$ Nuclear Magnetic Resonance Spectroscopy, Jordi Frigola et al.

Chemical Communications, 1968, 917–918, "The Crystal Structure of a Novel Heterocycle containing an Intramolecular Carbon–Nitrogen Hydrogen Bond", by Charles J. Fritchie et al.

J.C.S. Perkins II, 1978, 431, "Basicity of the Carbonly Group. Part 6, Calorimetric and Specto–metric Study of Complexation of para–substituted N–Ammoniobenz–amidates by Boron Trifluoride", by Jean–Francois Gal et al.

Intra–Science Chemistry Reports, vol. 5, No. 4, 1971, pp. 305–316 "Studies on the Biologically–Active Conformations of Angiotensin" by Garland.

J. Chem. Soc. (C), 1967, 2577–2580, Thermolysis of Trimethylamine–benzimide and Related Compounds: Identification of By–products and their Probable Mechanism of Formation by Martin S. Gibson et al.

Acta Chem. Scand. 9 (1955), No. 9, 1498–1509, "The Reaction of Hydrazine with Cinnamic Acid Derivatives", by W.O. Godtfredsen et al.

Polymer Letters, vol. 2, pp. 1095–1096 (1964), "Thermally Reversible Homopolymer Gel Systems", by Howard Haas et al.

Tetrahedron Letters, No. 26, pp. 1733–1737, 1964, "Beaktionen von Benzol–Derivaten Mit Nitrenen", by Klaus Hafner et al.

Lipids, vol. 20, No. 10 (1985), 685–692, "Hypolipidemic Activity of the Surfactants Aminimides, and Their Effects on Lipid Metabolism of Rodents", by Iris H. Hall.

Int. J. Peptide Protein Res. 21, 1983, 392–405, "Peptides containing dipropylglycine", by Paul M. Hardy et al.

Bull. Soc. Chim. Belg., 65, pp. 291–296, 1956, "Syntheses des isocyanates de vi2nyle et d'isoprpenyle", by R. Hart.

Journal of Fluorine Chemistry, 51, 1991 419–431, "Amine–(polyfluoroalkoxyacyl)imide Surfactants[1]", by Lisa Haywood et al.

"The Chemistry of 2–Alkenyl–2–Oxazolin–5–Ones" by Steven H. Heilmann et al.

Journal of Polymer Science, vol. 22, 3149–3160(1984), "Chemistry of Alkenyl Azlactones. IV. Preparation and Properties of Telechelic Acrylamides Derived from Amine–terminated Oligomers" by Steven M. Heilmann et al.

J. Am. Chem. So., 1982, 104, pp. 2437–2444, Solid–State and Solution Conformation of Homo Oligo ($\alpha$–aminoisobutyric acids) from Tripeptide to Pentapeptide: Evidence for a $3_{10}$ Helix$^{1a}$.

J. Med. Chem. 1991, 34, 1777–1789, "Synthesis, Conformational Properties, and Antibody Recognition of Peptides Containing $\beta$–Turn Mimetics Based on $\alpha$–Alkylproline Derivatives" by Mark G. Hinds.

J. Org. Chem., 24, 1825, vol. 28 (1959), "Alkyl–(alkoxyalkyl–)hydrazones", by John C. Howard et al.

University of Arizona, pp. 797–804, "Design of Drugs Acting at Peptidergic Receptors", by Victor J. Hruby.

Biopolymers, vol. 22, 517–530(1983), "Conformational and Dynamic Considerations in the Design of Peptide Hormone Analogs", by Victor J. Hruby et al.

Die Angewandte Makromolekulare Chemie 11 (1970) 109–124, "Syntheses und Reaktionen von 2–Alkenyloxazolonen" by Von Klaus Hubner et al.

Liebigs Ann. Chem. 1977, 506–527, "Additionen mit Chinolinium–, Isochinolinium– und Phenanthridinium–N–imid", by Rolf Huisgen et al.

Journal of the American Oil Chemists' Society, vol. 55, Feb. 1978, "Properties of 2–Hydroxyethylamine Acylimide Aqueous Solution—Unusual Clouding Phenomenon", Isao Ikeda et al.

Journal of the American Oil Chemists' Society, vol. 53, 1976, "Synthesis of 1,1,1–Tris(2–hydroxyethyl)amine–2–acylimide", by Isao Ikeda et al.

Organic Mass Spectrometry, 1971, vol. 5, pp. 61 to 71, "The Mass Spectra of N–Acyliminopyridinium and Isoquinolinium Betaines", by M. Ikeda et al.

The Chemical Society of Japan, No. 3, 1982, "Synthesis, Surfactant Properties and Catalytic Action of Crown Ethers Bearing Aminimide Group", by Seiichi Inokuma et al.

Journal of Polymer Science: Part A: Polymer Chemistry, vol. 25, 1363–1382 1987, "Thermal Decomposition Behavior of Bis–aminimides and Their Application to Polymerization of Epoxide" by Shinzo Inubushi et al.

Journal of Polymer Science: Part A: Polymer Chemistry, vol. 25, 137–150 (1987), "Thermal Decomposition Behavior of Mono–aminimides and Their Application to Polymerization of Epoxide", by Shinzo Inubushi et al.

Journal of Polymer Science, Part A:, Polymer Chemistry, vol. 26, 1779–1789 (1988), "Tough Epoxy Resins Cured with Aminimides", by Shinzo Inubushi et al.

Can. J. Chem., vol. 52, 1974, 3671–3675, "New Route to Cyclic Azomethine Imines", By P.C. Ip et al.

The Journal of Organic Chemistry, Aug. 31, 1966, "Synthesis of N–[1–(1–Substituted 2–oxopropyl)]acrylamides and –methacrylamides. Isolation and some Reactions of Intermediates of the Dakin–West Reaction", by Yosmo Iwakura et al.

Journal of Molecular Structure, 243 (1991) 365–368, "A Multinuclear NMR Study On Some Cyclic Aminimides and Related Compounds", by J. Jazwinski.

Biopolymers, vol. 22, 241–246(1983), "Stabilizing Effects of 2–Methylalaline Residues on $\beta$–Turns and $\alpha$–Helixes", by G. Jung.

Coyright 1981 by Walter de Gruyter Berlin, Structure and Activity of Natural Peptides, Properties of the Membrane Modifying Polypeptide Antibiotics Alamethicin and Trichotoxin A–40, by Gunther Jung.

Journal of the American Oil Chemists' Society, 52, 1975, "Aminimides: II. Antimicrobial Effect of Short Chain Fatty Acid Derivatives", by J.J. Kabara et al.

Chemistry Letters, pp. 413–414, 1976, "Synthesis and Characterization of 1–Imidoyliminopyridinium N–Ylides", by Akikazu Kakehi et al.

Chemical Abstracts, vol. 72, 1970, 45292–45293, "Reactive surfactants. II. Synthesis of 2–acyl–1,1,1–trimethylhydrazinium hydroxide inner salts and their properties", by E. Kameyama et al.

Nippon 1974, No. 9, 1789, "Preparation and Some Properties of (2–Hydroxyalkyl)–dimethylammonium–N–acylimine", by Eiichi Kameyama et al.

Chem. Phar. Bull., vol. 23, 1975, 452–455, "Studies on Ketene and Its Derivatives. LXVIII Reaction of Kiketene with N–Imino–pyridinium, –quinolinium, and –isoquinolium Ylides", Tetsuzo Kato et al.

Gazzetta Chimica Italiana, 117, 1987, 509–511, "The Structure of the Pyridine 1–Benzimide Mono Cation", by Alan R. Katritzky.

Tetrahedron, vol. 36, pp. 679 to 699, "Conversions of Primary Amino Groups Into Other Functionality Mediated by Pyrylium Cations" by Alan R. Katritzky.

J.C.S. Perkin I, 1979, "Heterocycles in Organic Synthesis. Part 17. Conversion of Primary Amines into Bromides and Chlorides", by Alan R. Katritzky et al.

J.C.S. Perkin I, 1979, "Heterocycles in Organic Synthesis. Part 19, Thermolysis of Pyridinium N–Acylimines: a New Preparation of Isocyanates", by Alan R. Katritzky et al.

J.C.S. Perkin I, 1979, "Heterocycles in Organic Synthesis, Part 16, The Conversion of Aliphatic Aromatic, and Heteroaromatic Primary Amines into Iodides" by Alan R. Katritzky et al.

J.C.S. Perkin I, 1979, "Heterocycles in Organic Synthesis. Part 24. A New Synthesis of NN'–Diarylcarbodi–imides", by Alan R. Katritzky et al.

Angew: Chem. Int. Ed. Engl. 23 420–429, 1984, Pyrylium Mediated Transformations of Primary Amino Groups into Other Functional Groups, by Alan R. Katritzky et al.

J.C.S. Perkin I, 1981, 1495–1500, "Reactions of Pyryliums with Mono–and asym–Di–substituted Hydrazines" by Alan R. Katritzky et al.

Heterocycles, vol. 18, 1982, "Pyrazolo(1,5–c)Pyrimidines from pyrylium Salts and Amidrazones and Pyridine Imidoyl–N–Imides from Imidoyl Chlorides", by Alan R. Katritzky et al.

J. Am. Chem. Soc. 1991, 113, 2275–2283, "Topographic Design of Peptide Neurotransmitters and Hormones on Stable Backbone Templates: Relation of conformation and Dynamics to Bioactivity" by Wieslaw M. Kazmierski et al.

J. Org. Chem., 1981, 46, 2490–2497, Relative Reactivity and Structures of Benzoyltrimethylhydrazine and 1–Benzoyl–2–methylpyrazolidine, by Spencer Knapp.

Journal of Polymer Science: Poylmer Chemistry Edition, vol. 21, 3597–3600 1983, "Synthesis of Polymers Containing Pyridinium Ylide and Iminopyridinium Ylide Structure", by S. Kondo et al.

Chem. Berg. 103, 2052–2016 (1970), Umlagerung von quartaren Allyl–, Benzyl– und Propargyl–hydraziniumsalzen, by Karl–Heinz Konig et al.

Tetrahedron, vol. 38, No. 14, pp. 2165–2181, 1982, "Syntheses von 2–Methylalanin–Peptiden, die pH–Abhangigkeit Ihrer $^{13}$C–NMR–Spektren und Eine Neue Methode Zur Auswertung uber CS–Diagramme," by Dieter Leibfritz.

Chemica Scripta. 1978–79, 13, 195–196, "Electron Deficient Heteroaromatic Ammonioamidates, 20[1]; N–(3–Quinazolinio)amidates, 8[1]", by M. Lempert–Sreter, et al.

J. Chem. Soc. Perkin Trans. 1 1983, "Electron Deficient Heteroaromatic Ammonioamides., etc.", by Magda Lempert–Sreter et al.

Tetrahedron, 1960, vol. 11, pp. 39 to 51., "Synthesis of Peptides Derived From Alpha–Methylalanine", by M.T. Leplawy et al.

Helvetica Chimica Acta—vol. 65, Fasc. 1 (1982)–Nr. 18, "18. Azimine. VI. $^{12}$) 1–Alkoxycarbonyl–2,3–dialkyl–und –2,3–diaryl–azimine" by von Christian Leuenberger.

Monatshefte fur Chemie, 120, 749–758 (1989), "1–Amino–2–hydrazinopyrimidin–N–ylides. Unusual Tautomers of 1–Aminopyrimidin–2–hydrazones", by Jurgen Liebscher.

J.C.S. Perkin, Trans 2, 1977, 909–914, "Mono– and Di–protonation Sites in N–Ammonio–amidates: a Specro–scopic Study", by Milica Liler.

J.C.S. Perkins II, 1980, 380, "The Kinetics of Hydrolysis of N–Trimethylammonioacetamide and of Substituted N–Trimethylammoniobenzamides in Concentrated Sulphuric Acid", by Milica Liler et al.

J.C.S. Chem. Comm., 1975, 93–94, "Methylation and Protonation Sites in Some N–Ammonioamidates" by Milica Liler et al.

Tetrahedron Letters No. 30, 2621–2624, 1974, "A convenient Thermal Route to N,N–Dialkylaminoisocyanates", by William J.S. Lockley.

Tetrahedron Letters No. 48, 4263–4266, 1974, "Cyclic Aminimides Containing The pyrazolone Skeleton", by William J.S. Lockley.

Canadian Journal of Chemistry, vol. 50, 1972, "Reaction of Diphenylcyclopropenethione with Pyridinium Imines", by J.W. Lown et al.

Tetrahedron Letters No. 5., 425–428, 1971, "Cycloadditions of Aminoisocyanates to Heterocumulenes", by Walter Lwowski et al.

Supplement II to Circulation Research, vols. XXX and XXXI, Sep. 1972, pp. 143–150, "Angiotensin II—Studies on the Biologically Active Conformation", by Garland R. Marshall, et al.

Plastics Manufacturing., vol. 83, 1975, "Amine imides" by Kanji Matsueda et al.

Liebigs Ann. Chem. 1980 715–724, "Die Kristallstruktur von α(tert–Butyloxycarbonylamino)–isobuttersaure" by Wilfried Mayr et al.

Canadian Journal of Chemistry, vol. 45, 1967, Aminimides. I. "A General Synthesis of Aminimides From Acyl Hydrazides and Their Pyrolysis", by William J. McKillip.

Canadian Journal of Chemistry, vol. 45, 1967, 2619–2622, "Aminimides. II. A one–step synthesis of aminimides from carboxylic acid esters", by William J. McKillip.

Chemical Reviews, 1973, vol. 73, No. 3, pp. 255–281, "The Chemistry of Aminimides", by W.J. McKillip et al.

Chemical Abstracts, vol. 114, 1991, p. 40, "Antiarrhythmic effect of adaptive activation of the vagal system and a new synthetic acetylcholine analog", by F.Z. Meerson.

Journal of Polymer Science: Polymer Chemistry Edition, vol. 21: 1159–1164 1983, Synthesis of Aminimide Monomers and Polymers, Avinash C. Mehta et al.

Structural Biology, 348–350, "Peptidomimetics in the study of opiate peptides", by Dale F. Mierke et al.

Journal of Polymer Science: Part A: Polymer Chemistry, vol. 29, 29–37(1991), "Copolymers of 2–Vinyl–4,4–Dimethylazlactone with Styrene and Ethyl α–Hydroxymethylacrylate" by Jeno Muthiah et al.

Ace. Chem. Res. 1981, 14, pp. 356–362, "Alamethicin, a Transmembrane Channel" by Ramakrishnan Nagaraj et al.

Acc. Chem. Res. 1981, 14, 356–362, "Alamethicin, a Transmembrane Channel", Ramakrishnan Nagaraj et al.

Journal of the American Chemical Society, 101:1, Jan. 3, 1979, "Stereochemically Constrained Linear Peptides. Conformations of Peptides Containing α–Aminoisobutyric Acid", by R. Nagaraj et al.

Acta Cryst. (1980), B36, 1498–1500, "Structure of a Peptide Oxazolone: 2–(1'–Benzyloxycarbonylamino–1'–methylethyl)–4, 4–dimethyl–5–oxazolone", by C.M.K. Nair et al.

Tetrahedron Letters, vol. 30, No. 49, pp. 6845–6848, 1989, "Asymmetric Synthesis of Unusual Amino Acids: Synthesis of Optically Pure Isomers of α–methyltyrosine", by Ernesto Nicolas.

Journal of Applied Polymer Science, vol. 27, 2361–2368 1982, "Aminimide as Hardener/Curing Promoter for One Part Epoxy Resin Composition", by Hideki Niino et al.

Chem Pharm Bull, vol. 11 (1963), pp. 774–748, "Pyridazine Derivatives IV. The Structures of Aminopyridazines", by Yoshiro Nitta.

Journal of Applied Polymer Science, vol. 27, 2361–2368 (1982), "Aminimide as Hardener/Cruing Promotor for One Part Epoxy Resin Composition", by Hideri Nhno and Saburo Noguchi.

Chem. Pharm. Bull., vol. 11, 9163), "Reaction of N–Aminopyridinium Derivatives. II. The Reactions of 1–(N–Acylalkylamino)pyridinium Salt Derivatives with Cyanide Ion. (A New Synthesis of Primary Amines)", by Tohsihiko Okamoto et al.

Chem. Pharm. Bull., vol. 14(5) 518–523, 1966, "Reaction of N–Aminopyridinium Derivatives.V. Syntheses of 1–(N–Methylacetamido)alkylpyridinium Salts and Their Reaction with Cyanide Ion", by Toshihiko Okamoto et al.

Tetrahedron, vol. 41, No. 12, 2239–2329, 1985, "Heterocyclic Mesomeric Betaines", by W. David Ollis.

J. Am. Chem. Soc., vol. 103, No. 11, 1981, pp. 2948–2955, "Sensitivity of Polypeptide Conformation to Geometry. Theoretical Conformational Analysis of Oligomers of – Aminoisobutyric Acid", by Yvonne Paterson et al.

J. Org. Chem., 1982, 47, 5023–5025, Degradation of Aminimides Obtained from Enamines and (Ehoxycarbonyl)nitrene, by Lucio Pellacani et al.

Journal of Molecular Structure, 86 (1982) 341–347, "Quantum Theory of the Structure and Bonding in Proteins", by David Peters and Jane Peters.

J.C.S. Dalton I, 1978, 1155, "Reactions of 2–Azidopyridine and 1–Pyridinio Ylides with Transition–metal Complexes", by Maddalena Pizzotti.

The Journal of Organic Chemistry, vol. 33, No. 10, Oct. 1968, "Bridgehead Nitrogen Heterocycles. I. A Convenient Synthesis of Pyrazolo[1,5–a]pyridines", by K.T. Potts et al.

J. Chem. Soc., Perkin Trans. 1 1983, 417–421, "Molecular Structure of Boc–Aib–Aib–Phe–Met–$NH_2$ DMSO. A Fragment of a Biologically Active Enkephalin Analogue", by B.V. Venkataram Prasad, et al.

Tetrahedron Letters No. 37, 3249–3252, 1974, "Cyclic Aminimides Containing the 3–oxo–5–Thioxo–1,2,4–Triazolidine Skeleton: Rearrangements of 5–Thiourazole Derivatives", by V.T. Ramakrishnan.

Biochemical and Biophysical Research Communications, pp. 898–904, Hydrophobic Channels in Crystals of an χ–Aminoisobutyric Acid Pentapeptide, by Ch. Pulla Rao.

Biochemical and Biophysical Research Communications, vol. 103, No. 3, 1981, pp. 898–904, "Hydrophobic Channels in Crystals of an x–Aminoisobutyric Acid Pentapeptide", by Ch. Pulla Rao et al.

Biopolymers, vol. 21, 2461–2472 (1982), "Molecular Structure of t–Butyloxycarbonyl–Leu–Aib–Pro–Val–Aib–Methyl Ester, a Fragment of Alamethicin and Suzukacillin: a $3_{10}$–Helical Pentapeptide", by Ch. Pulla Rao et al.

pp. 33–34, "Multiazlactones—Potential Alternatives to Isocyanate and Epoxy Resins"by Jerald K. Rasmussen.

Makromol. Chem., Rapid Commun. 5,67–70 (1984), "Chemistry of Alkenylazlactones, $2^{a)}$ Reaction with thiols", by Jerald K. Rasmussen et al.

J. Heterocyclic Chem., 27, 1041 (1990), "Synthesis of Some N–[Pyridyl(phenyl)carbonylamino]–alkyl–1,2,3,6–tetrahydropyridines", by Kinfe K. Redda.

J. Med. Chem., 1979, vol. 22, No. 9, 1079, "Syntheses of N–Substituted 2(3,4)–Pyridylcarboxylic Acid Hydrazides with Analgesic and Antiinflammatory Activity", by Kinfe Redda et al.

Journal of Pharmaceutical Sciences, vol. 81, No. 5, May 1992, "Synthesis and Pharmacological Evaluation of Some N–[Pyridyl(phenyl)carbonylamino]methyl–1,2,3,6–tetrahydropyridines" by Kinfe K. Redda et al.

Chem. Pharm. Bull. 39 (3) 786–791 1991, "Synthesis and Anti–inflammatory Activities of Some N–[Pyridyl(penyl)carbonylamino]–tert–butyl/phenyl–1,2,3,6–tetrahydropyridines" by Kinke K. Redda et al.

Nature, vol. 300, Nov. 1982, pp. 325–330, Articles—"A voltage–gated ion channel model inferred from the crystal structure of alamethicin at 1.5–A resolution", by Robert O. Fox, Jr. & Frederic M. Richards.

Tetrahedron, vol. 49, No. 18, pp. 3767–3780, 1993, "Electrophilic Amination of Pyrimidine–2–thiones – Synthesis of Zwitterionic 2–Aminothiopyrimidinium–N–ylides, Pyrimidine–2–ones and Bicyclic Pyrimidinium Compounds", by Beate Riemer et al.

Acta Cryst. (1983), C39, 894–896, "tert–Butyloxycarbonyl–α–aminoisobutyryl–α–aminoisobutyrate Benzyl Ester, $C_{20}H_{30}N_2O_5$", by Patrick Van Roey et al.

Int. J. Peptide Protein Res. 19, 1982, 499–505, "Crystal and molecular structure of tert.–butyloxycarbonyl–L–hydroxy–prolyl–α–aminoisobutyryl–α–aminoisobutryl–L–phenylalaninol" by Patrick Van Roey et al.

Biopolymers, vol. 32, 407–410 (1992), "Peptidomimetics as Receptors Agonists or Peptidase Inhibitors: A Structural Approach in the Field of Enkephalins, ANP and CCK" by Bernard P. Roques.

Tetrahedron Letters No. 52, pp. 4859–4862, 1976, "Regiospecific Versus Non–Regiospecific Photoinduced Ring–Enlargement of 3–Substituted 1–Iminopyridinium Ylides", by Jacques S. et al.

M.R.Chemistry, vol. 20, 1988, 471–474, "Synthesis and Spectroscopic Studies of 2–(1,1–Dimethylhydrazono)propyl Phosphonates" by Miguel Salazar et al.

The Journal of Organic Chemistry, vol. 35, No. 2, Feb. 1970, The Chemistry of Diazepines. The Photochemical Intramolecular 1,3–Dipolar Cycloaddition of Substituted 1–Ethoxycarbonyliminopyridinium Ylides, Tadashi Sasaki, et al.

Journal of Chemistry, 31, Nov. 1966, 3851–3852, "A Novel Synthesis of 1,5–Diphenylpyrazolone–3", by Henry W. Schiessl et al.

J. Prakt. Chem. [2] 110, 204, 1925, "Polyspirocyclische Komplexe des Palladiums mit Phosphor–Yliden", by Hubert Schmidbaur et al.

Liebigs Ann. Chem. 1982, 1304–1321, "The α–Helical Conformation of the Undecapeptide Boc–L–Ala–[Aib–Ala]$_2$–Glu(OBzl)–Ala–[Aib–Ala]$_2$–OMe: Synthesis, X–Ray Crystal Structure, and Conformation in Solution", by Heribert Schmitt.

Liebigs Ann. chem. 1988, 1025–1031, "Asymmetric Synthesis of Boc–L–Val–(R)–α–MePro–OMe, Boc–L–Val–(R)–Proome, and of Boc–L–Val–(R)–α–MePhe–OMe, Ac–L–Val–(R)–α–MePhe–OMe and Their Analogues. A New Strategy for the Synthesis of Non–Proteinogenic Dipeptides", by Ulrich Schollkopf.

Communications, Dec. 1981, pp. 969–971, Asymmetric Syntheses via Heterocyclic Intermediates; VIII. Enantioselective Synthesis of (R)–α–Methyl–α–amino Acids using L–Valine as Chiral Auxiliary Reagent by Ulrich Schollkopf et al.

Angew. Chem., 90 (1978), Nr. 2, pp. 136–138, "Asymmetrische Synthesen von x–Alkyl–x–aminocarbon–sauren durch Alkylierung von 1–chiral–substituierten 2–Imidazonin–5–onen", by Von Ulrich Schollkopf et al.

Angew Chem. Int. Ed. Engl. 18 (1979), No. 11, Enantioselective Synthesis of α–Methyl–αaminocarboxylic Acids by Alkylation of the Lactim Ether of cyclo–(l–ala–l–Ala), by Ulrich Schollkopf et al.

Angew, Chem. Internat. Edit., vol. 14(1975), No. 8, "Applications of Field Desorption Mass Spectrometry in Inorganic Chemistry: Salts", by H.R. Schulten.

J. Org. Chem USSR, 1977, 13, 885, "Reaction of Acyl Nitrenes with Unsaturated Compounds", by V.P. Semenov et al.

Tetrahedron Letters, vol. 27, No. 52, pp. 6319–1986, "Cyclic Carbalkoxy Aminimides. Synthesis and Thermal Decomposition To Give N, N–Dimethylamino Isocyanate", by Jean–Pierre Senet.

Biophy.J., vol. 64, Apr. 1993, 1017–1028, "The permeation properties of small organic cations in gramicidin A channels", by Sang–Ah Seoh.

J.C.S. Chem. Comm., 1978, pp. 996–997, "The $3_{10}$ Helical Conformation of a Pentapeptide Containing a–Aminoisobutyric Acid (Aib): X–Ray Crystal Structure of Tos–(Aib)$_5$–OMe", by N. Shamala et al.

Biochemical and Biophysical Research Communications, vol. 79, No. 1, 1977, "The Crystal and Molecular Structure Of The Amino Terminal Tetrapeptide of Alamethicin. A Novel 310 Helical Conformation", by N. Shamala et al.

J.C.S. Chem.Comm., 1978, 996–997, "The $3_{10}$ Helical Conformation of a Pentapeptide Containing α–Aminoisobutyric Acid (Aib): X–Ray Crystal Structure of Tos–(Aib)5–OMe" by Narayanaswamy Shamala et al.

I–Pharmacology, vol. 108, 1988, p. 31589, "Regulation of carnitive–dependent metabolism of fatty acids in myocardium under the influence of 3–(2,2,2–tri–methylhydrazinium)propionate" Zh. Shutenko et al.

Chemical Abstracts, vol. 115, 1991, p. 45, "Regulation of the carnitive–dependent metabolism of fatty acids in the rat myocardium", Zh. Shutenko et al.

The Journal of Organic Chemistry, vol. 33, No. 4, Apr. 1968, "Aminimides. VI. Synthesis of Aminimides from Carboxylic Acid Esters, Unsymmetrically Disubstituted Hydrazines, and Epoxides", by R.C. Slagel.

Canadian Journal of Chemistry, vol. 45, 2625, (1967), "Aminimides. III. A convenient synthesis of isopropenyl isocyanate", by Robert C. Slagel et al.

Organic Preparations and Procedures Int. 13(1), 55–58, 1981, "Preparation of 2–Hydroxyethyldimethylamine Acylimides" by Robert J. Small.

The Journal of Organic Chemistry—Notes 851–855, "Reactions of Hydrazines with Esters and Carboxylic Acids" by Richard F. Smith.

J. Org. Chem., vol. 41, No. 9, 1976, 1555–1556, "Reaction of 1,1–Dibenzoyl–2,2–dimethylhydrazine with Methyl p–Toluenesulfonate", by Richard F. Smith.

J. Am. Chem. Cos., 1981, vol. 103, pp. 1493–1501, "Crystal Structures and Conformational Calculations of Fragments of Alamethicin Containing Aminoisobutyric" by G. David Smith.

Chemical Communications, 1965, 120, "The Pyrolysis and Photolysis of Trimethylamine Benzimide", by Richard F. Smith.

J. Org. Chem., vol. 59, No. 14, 1974, "Stevens Rearrangement of Carbamoylaminimides" by Richard F. Smith et al.

Chemistry Department of the University of Michigan, Sep. 1959, 1325–1332, vol. 24, "Nitroative Cleavage of N',N'–Dialkylhydrazides and Tertiary Amines", by Peter Smith et al.

Bull. Soc. Chem., France—1969 No. 6, 2175–2179, "No. 382—Syntheses Photochimique de (1–H)–Diazepines–1,2" by Jacques Streith et al.

Chem. Ber. III, 780–790 (1978), "Pyrazolium–Betaine aus 1, 1–Dialkylhydrazinen und Acetylencarbonsaureestern", by Wolfgang Sucrow et al.

Journal of the American Chemical Society, 90:19, Sep. 11, 1968, "Novel Heterocyclic Syntheses from Azomethine Imides. 2–Unsubstituted Diazetidinones", by Ken'ichi Takeuchi, et al.

Chem. Pharm. Bull., vol. 31, 1983, 1378–1381, "1,3–dipolar Cycloaddition Reaction of 1–Methylperimidine 3–Ylides with Dimethyl Accetylenedierboxylate", by Yasumitsu Tamura et al.

J. Heterocyclic Chem., 9, Aug. 1972, 865, "Synthesis of 3–substituted N–Aminopyridinium Salts(I)", by Yasumitsu Tamura et al.

J.C.S. Perkin I, 1973, 2580–2583, "Synthesis and Thermal Reaction of 2,2–Diacyl–N–(1–pyridinio)vinyl–aminides: Formation of Pyrazolo[1,5–a]pyridines and Isoxazoles", by Yasumitsu Tamura et al.

Chem. Pharm.Bull., 19(6)1285–1286 1971, "The Photo Arrangement and Thermolysis of N–Benzoylimino–isoquinolinium and Quinolinium Betaines", by Yasumitsu Tamura et al.

Organic Preparations and Procedures 1(3), 217–219 (1969), "A convenient synthesis of 5–oxazolones. 2–phenyl–5–oxazolone" by Lloyd D. Taylor et al.

Polymer Letters, vol. 7, pp. 597–603(1969), "The Synthesis of Vinyl Peptide Monomers", by L.D. Taylor et al.

Journal of Polymer Science: Part C: Polymer Letters, vol. 24, 287–289 (1986), A Polymer whose Aqueous Solutions Show the Properties of Negative Thixotropy and Thermoreversible Gelation: (Poly–(Trimethylamine p–Vinylbenzimide), by LLoyd D. Taylor et al.

Organic Preparations and Procedures 1(3), 217–219(1969), "A convenient Synthesis of 5–oxazolones. 2–Phenyl–5–oxazolone", by L.D. Taylor et al.

Makromol Chem., Rapid Commun. 3, 779–782(1982), "Synthesis of Poly(4,4–dimethyl–2–vinyl–5–oxazolone) an Interesting Material for Preparing Polymeric Agents", by Lloyd D. Taylor et al.

Polymer Letters, vol. 9, pp. 187–190(1971), "Synthesis and Polymerization of 2–vinyl–4,4–Dimethyl–5–Oxazolone" by L.D. Taylor et al.

Rubber Chem. Technology, 53, 1980, "Halogen–containing Aminimide Compounds as Tire Cord Adhesives", by P.E. Throckmorton et al.

Eur. J. Med. Chem.—Chem. Ther. 1982–17, N. 3, pp. 265–270, "Aminimides ethyleniques a action vasodilatatrice peripherique", by Mohamed Tichniouin et al.

Eur. J. Med. Chem., 1982, 17, No. 3, pp. 265–270, "Aminimides ethyleniques a action vasodilatatrice peripherique", by M. Tichniovin et al.

J. Chem. Soc. Perkin Trans. 1988, "Reactions of Some 1,3–Diaminonucleophiles with Azlactones" by Ahmad M. Tikdari et al.

Int. J. Peptide Protein Res. 22, 1983, 603–610, "Bioorganic stereochemistry", by Claudio Toniolo et al.

Biopolymers, vol. 22, 205–215(1983), Preferred Conformations of Peptides Containing α,α–Disubstituted α–Amino Acids, by Claudio Toniolo et al.

Bull Chem. Soc. Japan, 1980, 53, 1149, "Reaction of Ethyl Aziodoformate with Morpholines", by Teruko Tshuchida et al.

J. Chem. Soc., Chem Commun., 1982, 875–876, "Evidence for Amide Resonance observed in Cyclic N–Ammonio–imitates by X–Ray Photoelectron Spectroscopy", by Shinji Tsuchiya.

J. Chem. Soc. Perkin Trans. 11, 1993, "On the Nature of Nitrogen–Nitrogen Bonding in Cyclic Aminimides", by Shinji Tsuchiya.

Chem. Pharm. Bull. 31(12)4568–4572 1983, "Thermal Rearrangements of Cyclic Amine Ylides. III.[1)] Intramolecular Cyclization of 2–Ethynylpyridine N–Imides to 3–Azaindolizine Derivatives", by Takashi Tsuchiya et al.

J. Org Chem., vol. 44, No. 16, 1979, 2850–2855, "On the Bond Character of N–Containing Ylides", by Shinji Tsuchiya et al.

Chem. Pharm. Bull., 30 (10)3757, 1982, "Studies on Diazepines. XVIII. Photochemical Synthesis of 3H–1,3–Benzodiazepines from Quinoline N–Acylimides", by Takashi Tsuchiya et al.

Bull Chem. Soc. Japan, 1983, 2073, "Double Cycloaddition Reaction of Imidazolium Methylides. Intermolecular 1,3–Dipolar and Intramolecular Diels–Alder Cycloaddition Reactions", by Otohiko Tsuge et al.

Biopolymers, vol. 20, 1123–1136, "X–Pro Peptides: Solution and Solid–State Conformation of Benzyloxycarbonyl–(Aib–Pro)$_2$–methyl Ester, a Type I β–Turn", by Y.V. Venkatachalapathi et al.

Journal of Chemistry, 1966, vol. 31, 1704–1707, "Cyclic Aminimides", by William S. Wadsworth, Jr.

Journal American Chemical Society, vol. 82, 1960, 5718–5721, "The Rearrangement of 1,1–Dimethyl–1–p–nitrobenzylamine–2–acetamide", by S. Wawzonek.

Journal of Chemistry, 28, 1963, vol. 28, 2376–2377, The Resolution of 1–Ethyl–1–methyl–1–p–nitrobenzylamine–2–acetamide, by S. Wawzonek et al.

J.Org.Chem., Sep. 1965, 3031–3033, "The Rearrangement of 1–Methyl–1–acetylimide–2–phenylpyrrolidine", by S. Wawzonek et al.

Organic Preparations and Procedures Int. 8(5), 215–217 (1976), "Electrolytic Preparation of bis–Dimethyl–2–Hydroxypropylamineazobenzimides", by S. Wawzonek et al.

J. Med. Chem., vol. 9, 852–857, "Central Nervous System Depressants. I. 1–Aminoalkyl–3–aryl Derivatives of 2–Imidazolidinone, 2–Imidazolidinethione, and Tetrahydro–2(1H)–pyrimidinone", by William B. Wright et al.

J. Med. Chem., 1982, 25, 720–723, "Synthesis of N–[[(Substituted–phenyl)carbonyl]amino]–1,2,3,6–tetrahydropyridines with Analgesic and Hyperglycemic Activity", by Jupita M. Yeung.

J. Med. Chem, 1987, 30, 104–108, "Synthesis of N–(3, 6–Dihydro–1(2H)–pyridinyl)benzamides with Hyperglycemic–Hypoglycemic Activity", by Jupita M. Yeung et al.

J. Med. Chem. 1982, 25, 191–195, "Synthesis of N–(Carbonylamino)–1,2,3,6–tetrahydropyridines with Analgesic, Antiinflammatory, and Hyperglycemic Activity", by Jupita M. Yeung et al.

Abstract. XP–002063092. Toko, Akira et al. "Photosensitive Resin Compositions".

Iwakura, Yoshio et al., "Synthesis of Polyamideamines form 5–Oxazolones". Journal of Polymer Science Part A–1, vol. 6, 785–791, 1968.

Markert, Gerhard et al., "Inhomogeneous Polymer Networks through Incompatibility". XP–002063091, p. 433.

Markert, Gerhard et al., "Inhomogene Netzwerke durch Unverträglichkeit". XP–002063090. pp. 199–212.

METHOD OF MAKING POLYMERS HAVING SPECIFIC PROPERTIES

This a continuation of application Ser. No. 08/290,720, filed Jun. 10, 1996, now U.S. Pat. No. 5,670,480.

FIELD OF THE INVENTION

The present invention relates to a novel method of controlled polymerization to produce encoded synthetic polymers, involving the stepwise assembly of discrete modules having selected structural features in a manner so as to produce a polymer having (1) a precisely ordered sequence of structural units; or (2) a precisely ordered sequence of structural units and a specific uniform chain length and molecular weight, depending on the particular strategy chosen; and (3) resultant physiochemical and biological properties which are the sum of the individual properties of the modules and their specific arrangement in the polymer.

BACKGROUND OF THE INVENTION

Existing polymerization methods fall into one of two basic types; (1) Addition or Chain Growth Polymerization; and (2) Condensation or Step-Growth Polymerization.

Chain growth polymerizations most commonly utilize monomers possessing reactive carbon-carbon double bonds, although other species, such as cyclic ethers, e.g., ethylene and propylene oxide and aldehydes, e.g., formaldehyde, can be polymerized in this way. These chain-growth polymerizations are characterized by the fact that the free radical, ionic or metal complex intermediates involved in the process are transient and can not be isolated. A generalized example for a simple free radical initiated vinyl polymerization is shown below:

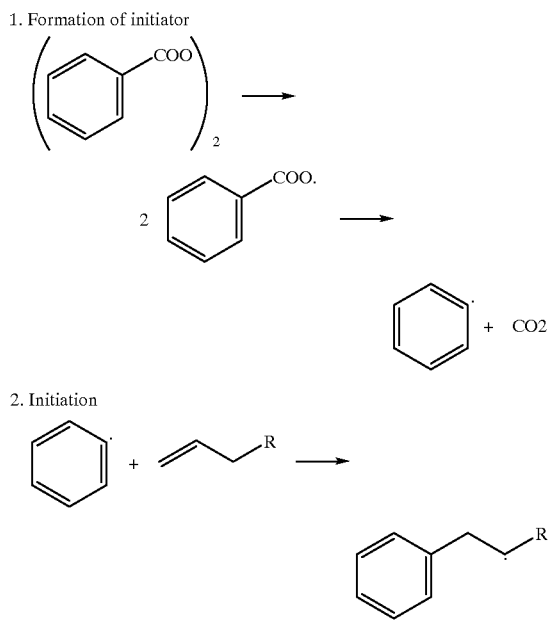

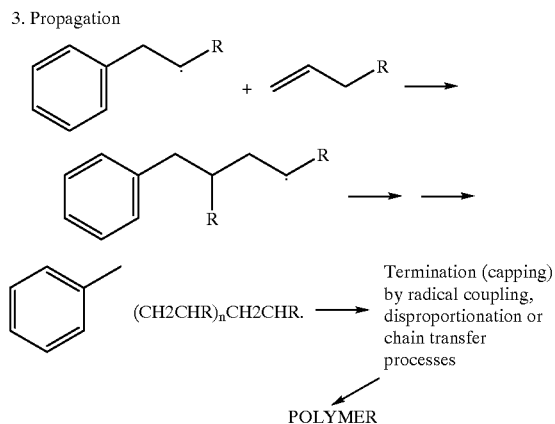

Step-growth polymerizations involve reactions which occur between molecules containing multiple reactive groups which can react with each other. An example of this is the well-known reaction of a glycol and a dibasic aromatic acid to give a polyester.

It can be readily seen that the use of multiple reactive monomers posessing groups with similar or equivalent reactivities with this method produces a mixture of individual polymer species having random arrangements of monomeric sequences and only statistical control of the resulting stoichiometric make-up.

While many different variations of these two classes of polymerization reaction schemes exist, e.g. initiation may be cationic, radical, anionic, sequential aldol, ring-opening or displacement, and many different reactive species may be employed, e.g. electron deficient alkenes, epoxides, polyamines, hydroxyesters, etc., all of these variations possess a common limiting feature—they all rely on a statistical or average stoichiometric control of the final polymeric product. This is achieved through the careful selection and control of the reaction conditions, such a concentration of monomers, agitation conditions, catalyst level, time/temperature cycles, etc. These existing polymerization methods do not have any ability to control the exact constitution or length of any specific individual polymer chain. The properties of the polymers produced via these processes are, in fact, a statistical average of the properties of a complex mixture of subtly differing individual polymer species having a range of molecular weights and containing differing combinations and sequences of monomers along the chains. Even in the simplest example of a step growth polymerization involving only two reactants, where the product is a polymer containing a single repeating structural motif, the product obtained will consist of a statistical mixture of a large number of individual molecules each having differing lengths and molecular weights.

In spite of these limitations, those skilled in the art have developed strategies by which these methods can be exploited. Average chain length can be controlled roughly by the ratio of initiator to monomer, or by quenching with an additive giving a range of molecular weights. Macroscopic properties can be modulated by the addition of comonomers which are incorporated randomly into the backbone.

However, these methods possess no ability to have discreet or even reproducible microsequence control, and the "address" of a singular functionality added to the polymerization reaction is statistically determined.

Most natural biological polymers, such as oligonucleotides, proteins and polysaccharides, on the other hand, contain precise sequences of monomer units which confer the polymer with highly specific functional properties, including a specific three dimensional structure. Recent advances in the understanding of the complex mechanisms of biochemical processes and of the underlying structure-function relationships of biological polymers involved in the replication (DNA—DNA), storage (DNA), transcription (DNA-RNA), translation (RNA-protein), communication, recognition, control (proteins, peptides, carbohydrates) and function (proteins, oligosaccharides) of all biological systems have illuminated the exquisite sensitivity of these polymers to microsequence variations. A classic example of this is sickle cell anemia which has been shown to be due to a single point mutation in the genetic sequence encoding for the beta chain of hemoglobin. As a result of this mutation, the abnormal hemoglobin contains a single valine in place of a glutamine in the sequence of the protein. This results in an abnormal shape for the hemoglobin, producing the characteristic sickle-shaped cells and the resulting tragic pathological consequences.

The biosynthesis of these biopolymers can be viewed, at a molecular level, to consist of a highly organized series of individual catenation steps, each carried out with specific reactants under highly controlled conditions and mediated by biocalytic agents, principally enzymes. All of the monomers necessary for the construction of these biological polymers are present in the vicinity of the reaction area and are carried by chaperone molecules to the site of their incorporation into the growing chain, where they are released and coupled. Since these polymers were designed by nature to carry out their highly specific functions under physiological conditions (water at pH 7 and physiological temperatures, etc.), and have been programmed by nature to be subject to natural biochemical transformations, such as proteolytic decomposition, they are usually not robust (notable exceptions include structural polymers such as chitin, cotton, skin, silk, hair and other structural materials) and are easily decomposed or denatured by exposure to non-physiological conditions, such as elevated temperatures, organic solvents, extremes of pH, etc. As a result, these molecules are generally ill suited for tasks other than their proper biochemical ones.

Simply put, the makers of polymers, while being able to statistically achieve good and consistent macroscopic properties in the polymeric materials which they produce, have not had any way, up to this point, to control the microscopic make-up of their product. Nature, in producing biomacromolecules, has evolved systems which allow exquisite control over both the microscopic make-up and the macro-structure of its functional polymers. However, these polymers are severely limited in the variety of uses to which they may be applied by their chemical constitution, their lack of stability towards chemical and biochemical agents and their sensitivity to changes in environmental conditions, such as temperature. In addition, the nature of natural scaffolds and substituents and their sensitivity to the chemical conditions necessary to manipulate and to transform them severely limits their utility in producing new materials from these components.

SUMMARY OF THE INVENTION

This invention relates to a method of making a polymer having specific physiochemical properties by forming a base module having a structure which includes at least two orthogonal reactivity or structural diversity elements suitable to impart a desired physiochemical property to a polymer which is made from said monomer; and reacting one or more modules to form a polymer having specific properties. The module is preferably an aminimide compound, an oxazolone-compound, or a derivative thereof. The module is prepared from first and second components which provide the orthogonal reactivity elements. The module may contain 2, 3, 4 or more orthogonal reactivity elements, depending on the desired performance properties of the resultant polymer.

The polymer chains are started with a terminus or starter module contains a single reactivity element and are capped at the desired point in the synthesis with a second terminus or capping module containing a single reactivity element in order to control the length of the chain.

The base module can be formed by reacting a first compound having at least one structural diversity element and a first reactive group, with a second compound having at least one structural diversity element and a second reactive group, wherein the first and second groups combine by an addition reaction.

Preferably, the first compound is produced by forming an oxazolone compound having at least one structural diversity element attached thereto and reacting it with a nucleophile or carbonyl compound which contains at least one structural diversity element to form a base module having one of the following structures:

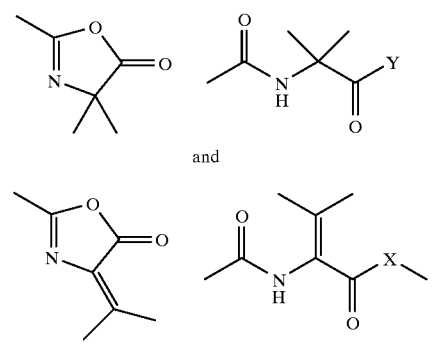

and wherein at least two of the unconnected lines are connected to structural diversity elements.

Alternatively, it is also preferred to provide the first compound as an aminimide-forming compound having at least one structural diversity element attached thereto and to react it with an oxazolone or an oxirane compound, which contains at least one structural diversity element to form a base module having one of the following structures:

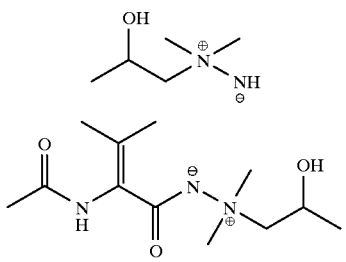

wherein at least two of the unconnected lines are connected to structural diversity elements.

In particular, this method can be used to make polymers having a designed water solubility. This invention still further relates to the polymers produced according to these methods. Still further, this invention relates to uniform polymers comprising a multitude of long chain molecules each of which have the same molecular weight and the same length.

This ability to produce polymeric chains of specific sequence and composition has great utility in the fabrication of a new generation of functional oligomeric and polymeric materials for a wide spectrum of applications, such as drugs, chiral recognition elements, catalysts, seperations tools, biomaterials, fibers, plastics, membranes, beads and gels.

DETAILED DESCRIPTION OF THE INVENTION

The present invention discloses a fundamentally new approach to the fabrication of oligomeric and polymeric molecules involving (1) the use of modular units which can contain at least two orthogonally reactive elements and are capable of bearing a wide variety of structural information, such as specific geometry, functionality, substituents, etc. (2) the stepwise assembly of polymers from these modules (a) by carrying out catenation or coupling reactions one step at a time or (b) by constructing "sub assemblies" of modular units one step at a time and connecting them together in a concerted manner in such a way that the resulting polymer has a controlled (encoded) microsequence and a resultant overall functional activity, which is the sum of the functional activities of the constituent modular parts. This approach involves the design and construction of a scaffolding superstructure, which sets the basic spacing and geometry of the molecule and serves to arrange and orient the attached substituent groups in a manner suitable to achieve the desired functional property and, simultaneously, serves to allow the incorporation of desired pendant substituents in the appropriate positions having the appropriate desired relationships to each other and to the scaffold to produce the desired functional effect in the final polymer.

In this application, the term "polymer" is used to refer to any catenated structure containing a sufficient number of modules to carry enough structural information to impart the desired property to the resulting polymer, usually consisting of a minimum of three monomers plus two terminus (starter and capping) modules.

A key element of this method is the presence of at least two orthogonal reactivity elements in the modules. Orthogonal reactivity elements are defined as those elements which are either (A) multiple reactive groups which are capable of being "turned on" independently of each other or (B) multiple differing reactive states which may be addressed or brought into being at different times or under different conditions in the catenation sequence. It is highly desirable, although not absolutely necessary, that the individual reactions be high-yielding addition reactions with no by-products, so that isolation and purification steps are not necessary between cycles. The two basic schemes are illustrated below:

A. Multiple Reactive Groups

Step 1. Coupling of "Starter Module" with "Extender Module"

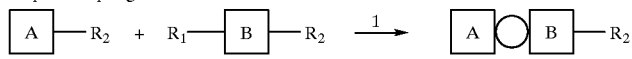

Step 2. Coupling of "Extender Module" with Chain

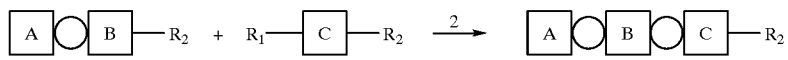

Step 3. Coupling of "Capping Module" with Chain

Where R1 and R2=groups capable of undergoing addition reactions with each other, and A, B, C, D are either monomeric modules or "sub assemblies" containing multiple modules stitched together in a sequence specific manner.

B. Multiple Reactive States

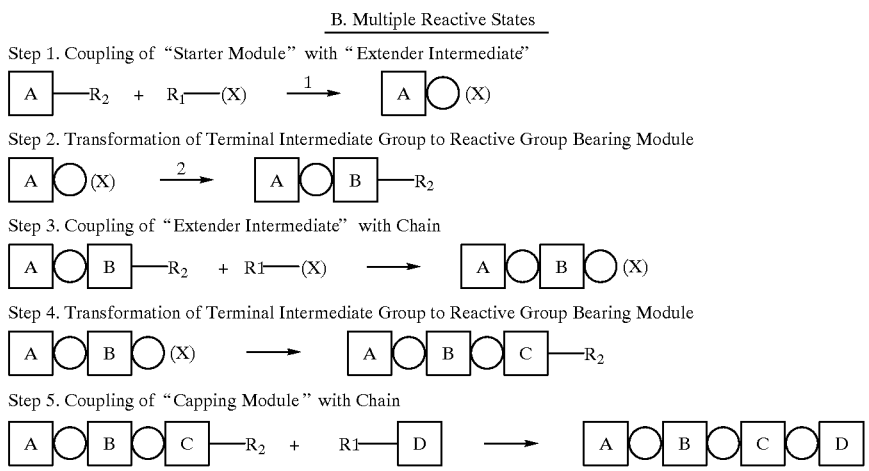

Where R1 and R2 are groups capable of undergoing addition reactions with each other, and A, B, C, D are either monomeric modules or "sub assemblies" containing multiple modules stitched together in a sequence specific manner.

These reactive orthagonalities allow each discrete addition reaction to be carried to completion before the next individual addition reaction is undertaken. If desired, the intermediate products may be isolated following each individual step. In this critical respect this method is fundamentally different from both chain and step-growth polymerization methods.

In addition to the stepwise sequential construction of polymers one unit at a time as illustrated, this method may be utilized to construct oligomeric "sub assemblies" having designed microsequences, and properties. These may then be connected together in a separate step to produce higher order assemblies, which may themselves again be connected together to, ultimately form a polymer having the desired set of properties. This strategy requires that one of the orthogonal reactivity elements on each sub-unit be either protected with an appropriate removable blocking group or contain a third orthogonally reactive group. These reactions may be carried out with modules containing >2 orthogonally reactive elements to produce three dimensionally cross linked networks and structures. Alternatively these sub assemblies may be combined with appropriately functionalized "classical" modules to produce hybrid polymers.

A new approach to the stepwise sequential construction of novel oligomeric and polymeric molecules is described. This approach involves the development of a process whereby molecular building blocks which contain appropriate atoms and functional groups and posses at least two orthogonally reactive elements are connected together in a stepwise sequential fashion to allow the modular assembly of oligomers and polymers with tailored properties; each module contributing to the overall properties of the assembled molecule. This approach to molecular construction is applicable to the synthesis of all types of molecules, including but not limited to mimetics of peptides, proteins, oligonucleotides, oligosaccharides, classical polymers, variants, hybrids of these and to fabricated structures and materials useful in materials science. It is analogous to the modular construction of a mechanical device that performs a specific operation wherein each module performs a specific task contributing to the overall operation of the device.

Examples of suitable modules containing appropriate orthogonally reactive elements for utilization in this method are given below:

Several of the specific modular chemistries chosen to illustrate and exemplify the invention are capable of bearing and maintaining chiral centers throughout the various steps involved. Where this is the case, the chirality will be shown. This is not intended to limit the scope of the invention to chiral materials, since there are a large number of variations and applications where structural stereocontrol is not required or where achiral materials are employed.

POLYMERS PRODUCED FROM OXAZOLONES

Oxazolone Modules

A type of oxazolone module appropriate for use in the present invention may be represented by the following general structure:

$$\underset{R^1 \quad R^2}{X \diagdown \underset{3}{\overset{2}{\bigcirc}}\underset{4}{\overset{O_1}{\diagup}}\overset{5}{\diagdown}O}$$

where R & R' are the same or different and X represents either a group having orthagonal reactivity to the oxazolone ring or a structural moiety, depending on which of two possible assembly strategies is chosen, as outlined below. $R^1$ and $R^2$ differ from one another and taken alone each signifies one of the following: alkyl including cycloalkyl and substituted forms thereof; aryl, aralkyl, alkaryl, and substituted or heterocyclic versions thereof; preferred forms of R1 and R2 are the side chain substituents occuring in native polypeptides, oligonucleotides, variants or mimetics of these, carbohydrates, pharmacophores, variants or mimetics of these, or any other side chain substituent which can be attached to a scaffold or a backbone to produce a desired interaction with a target system.

The substituents R & R' may be of a subset of hydrophilic substituents such as, but not limited to hydroxymethyl, hydroxyethyl, hydroxypropyl, thioethyl, thiomethyl; carboxymethyl, carboxyethyl, ethylcarboxamido, methylcarboxamido; aminomethyl, aminoethyl, aminopropyl, guanindinylpropyl, guanidinylbutyl; mono-, di-, and triaminobenzyl, mono-, di-, and trinitrobenzyl; mono-, di-, tri-, and tetrahydroxy benzyl, mono- or polyhydroxyaryl (e.g. pyrogallol); heteroaryl (e.g. alkylpyridines, imidazole, alkyltryptophans); alkyl nucleotides; all substituted pyrimidylalkyl and substituted purinealkyl moieties; mono-, di-, and oligosaccharide (e.g. N-methylfucosamine, maltose and the calicheamicin recognition sequence respectively); alkylsulfonates, alkylphosphonates; a-polyfluoroketones; secondary, tertiary and quaternaryamines; hydrazines and the hydrazinium salts R and R' may also come from the subset consisting of hydrophobic substituents such as, but not limited to: hydrogen; methyl, ethyl propyl, isopropyl, butyl, sec-butyl, isobutyl, tert-butyl, pentyl, iso-, sec-, and neopentyl, hexyl, heptyl, octyl, nonyl, decyl, etc.; vinyl, propenyl, butenyl or other alkenyl groups; acetylenic side chains; aromatic polycyclics (e. g. biphenyl, binaphthyl, naphthylphenyl, phenylnaphthyl); fused aromatic polycyclics (e.g. anthracene, phenylene, pyrene, acenaphthene, azulenes); fused polycyclics (e.g. decalin, hydrindanes, steroids); phenyl, alkylphenyl, phenylalkyl; benzyl, mono-, di-, tri-, and tetraalkylbenzyl; mono-, di-, and trialkoxybenzyl; heteroaryl (e.g. furyl, xanthanyl, quinolyl); methoxyalkyl, ethoxyalkyl, aryloxy; methylmercaptans, ethylmercaptans, alkyl thioethers and arylthioethers; dyes and fluorescent tags (such as rhodamine or fluorescein); alkyl esters, aryl esters, aralkyl esters, and alkylaryl esters.

Polymerization Strategies

These oxazolone modules may be employed to construct oligomers and polymers in two different ways:

A. Ring Opening Reaction/2-Position Substituent Addition

Oxazolones with suitable substituents at the 2-position (X=an orthogonally reactive group) may act as orthogonally reactive agents suitable for the construction of the polymers which are the subject of the present invention. This may be accomplished by carrying out alternating ring opening and 2-position substituent addition reactions with suitable bifunctionally reactive species. One terminus of these reactive elements should contain an SH, OH or NH group capable of underegoing ring-opening addition reaction with the oxazolone ring. The second terminus of the reactive element should contain a group capable of undergoing addition reaction with X. The choice of this second group, obviously, depends on the nature of the specific X group chosen in each case. Appropriate 2-position substituents include vinyl groups, which make the oxazolone a Michael acceptor, haloalkyl and alkyl sulfonate esters and epoxide groups. This is shown below for the case of alternating ring opening and Michael additions to the double bond of a 4,4-disubstituted-2-vinyloxazolone by appropriate dinucleophillic species produces polymeric chains, as shown

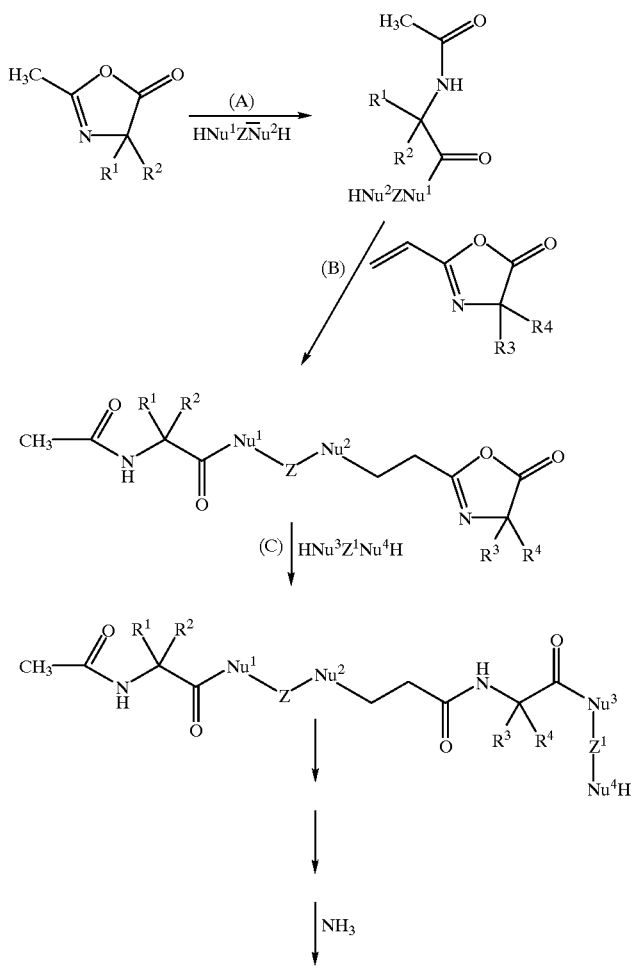

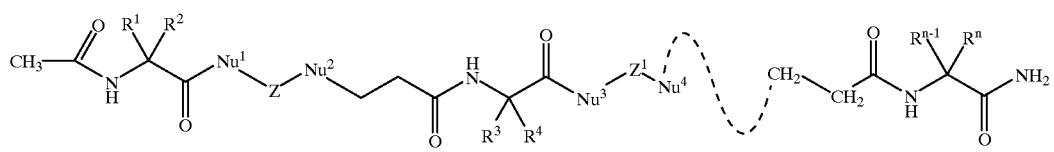

In the above sequence of reactions, $HNu^1$—Z—$Nu^2H$ represents a structure containing two differentially reactive nucleophilic groups, such as methylamino-ethylamine, 1-amino propane-3-thiol, and so on; groups $Nu^1$, $Nu^2$, $Nu^3$ and $Nu^4$ need not be identical and Z is a generalized structural group connecting HNu1 and HNu2. $HNu^1$—Z—$Nu^2H$ may contain two nucleophilic groups of differential reactivity, as stated above, or if $Nu^1$ and $Nu^2$ are of comparable reactivity one of the nucleophilic groups is protected to prevent it from competing with the other and deprotected selectively following acylation; protecting groups commonly used in the art of peptide synthesis (e.g., for the nucleophilic groups such as amino, hydroxyl, thio, etc.) are useful in the protection of one of the Nu substituents of the structure $HNu^1$—Z—$Nu^2H$. The product of the acylation reaction with $HNu^1$—Z—$Nu^2H$ (after Nu-deprotection, if necessary) is further reacted with a new oxazolone unit in a Michael fashion, and this addition is followed by ring opening acylation with an additional dinucleophile; repetition of this sequence of synthetic steps produces a growing polymeric molecule.

The Michael reaction step is usually carried out using stoichiometric amounts of nucleophile AXH and the oxazolone in a suitable solvent, such as toluene, ethyl acetate,. dimethyl formamide, an alcohol, and the like. The selectivities of the Michael and oxazolone ring-opening processes impose certain limitations on the choice of the nucleophiles shown above. Specifically, nucleophiles of the form ROH tend to add primarily via the ring-opening reaction, and usually require. acidic catalysts (e.g., BF3); thus, Nu2 should not be OH. Likewise, primary amines tend to add only via ring-opening, and Nu2 should therefore not be NH2. Secondary amines readily add to the double bond under appropriate reaction conditions. Nucleophiles of the form RSH will exclusively add via ring-opening if the sulfhydryl group is ionized (i.e., if the basicity of the reaction mixture corresponds to pH>9); on the other hand, such nucleophiles will exclusively add via Michael reaction under non-ionizing (i.e., neutral or acidic) conditions. During the Michael addition, it is important to limit the presence of hydroxylic species in the reaction mixture (e.g., moisture) to avoid ring-opening side-reactions.

The ring-opening reactions can be carried out either in an organic solvent such as methylene chloride, ethyl acetate, dimethyl formamide (DMF) or in water at room or higher temperatures, in the presence or absence of acids, such as carboxylic, other proton or Lewis-acids, or bases, such as tertiary amines or hydroxides, serving as catalysts.

An example of the application of this strategy is given below for the synthsis of a subunit containing four structural modules and the subsequent assembly of these modules into a polymer containing repeating sequences of these specific subunits:

The required 4,4'-disubstituted oxazolone modules may be prepared from the appropriate N-acyl amino acid using any of a number of standard acylation and cyclization techniques well-known to those skilled in the art, e.g.:

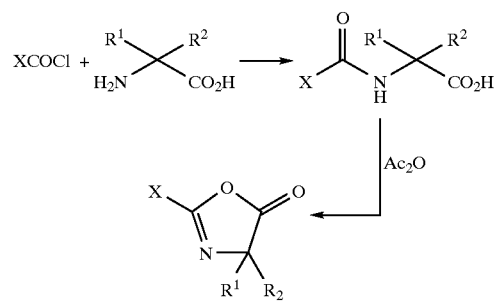

Alternative reactive groups may be introduced at the 2-position of the oxazolone in this way, as shown for a benzyl substituted reactive substituent:

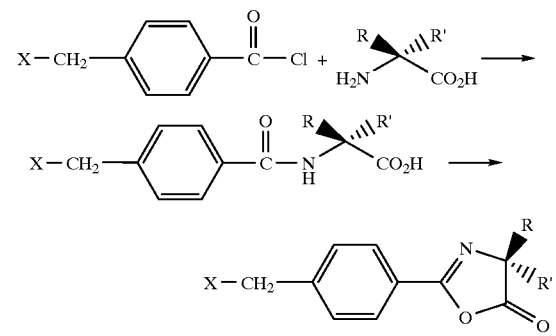

A wide variety of 4-monosubstituted azlactones may be readily prepared by reduction of the corresponding unsaturated derivatives obtained in high yield from the condensation reaction of aldehydes, ketones, or imines with the oxazolone formed from an N-acyl glycine (49 *J. Org. Chem.* 2502 (1984); 418 *Synthesis Communications* (1984))

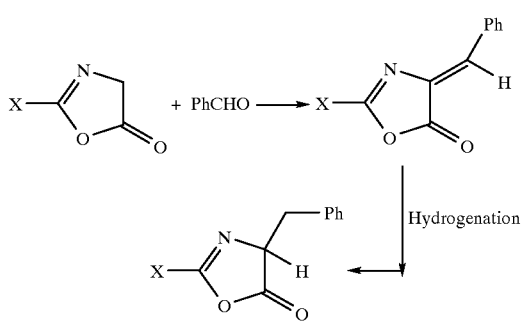

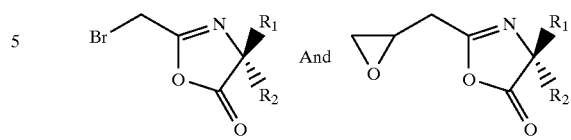

Other important bifunctionally reactive oxazolone derivatives which may be employed in these schemes include:

B. Alternating Sequences of Nucleophilic Oxazolone-Ring-Opening Addition Reactions Followed by Oxazolone-Forming Cyclization Reactions

Alpha,Alpha'-Disubstituted Sequences

According to this approach, oxazolone modules are catenated via ring-opening nucleophilic attack by the amino group of an alpha,alpha'-disubstituted amino acid; the resulting adduct is subsequently recyclized to form a terminal oxazolone (with retention of chirality). This is then subjected to another nucleophilic ring-opening catenation reaction, producing a growing polymer as shown below. This procedure is repeated until the desired polymer is obtained.

These may be converted to 4,4'-disubstituted oxazolones by alkylation of the 4-position, as in the following transformation (*Synthesis Commun.*, Sept. 1984, at 763; 23 *Tetrahedron Lett.* 4259 (1982)):

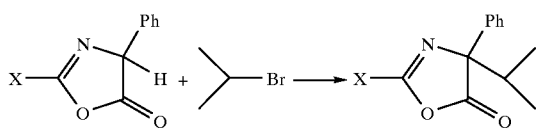

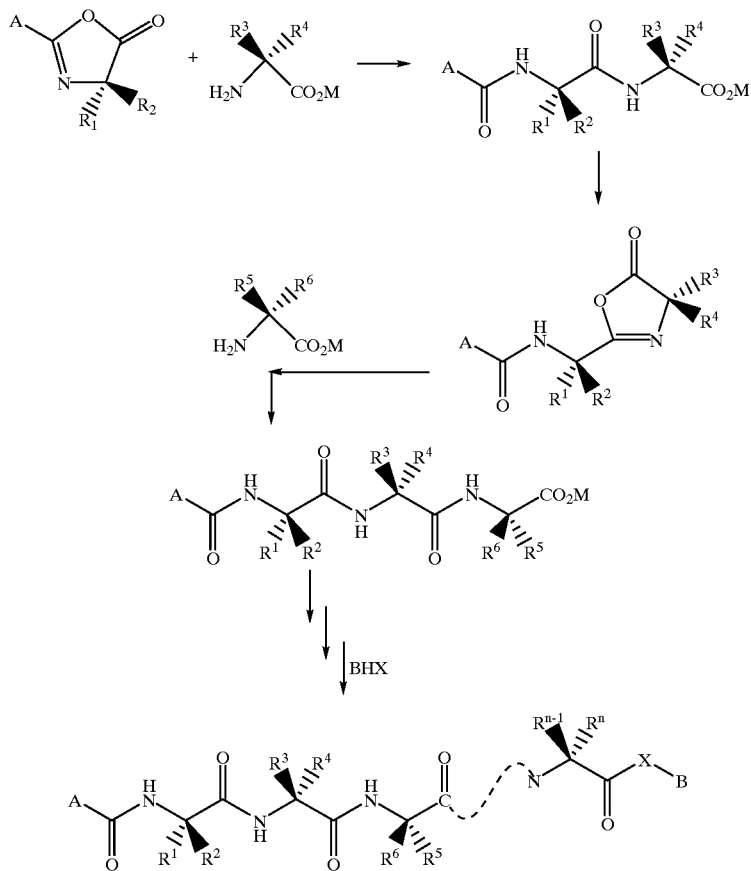

Wherein M is an alkali metal; each member of the substituent pairs $R^1$ and $R^2$, $R^3$ and $R^4$, and $R^5$ and $R^6$ differs from the other and taken alone each signifies alkyl, cycloalkyl, or substituted versions thereof, aryl, aralkyl or alkaryl, or substituted and heterocyclic versions thereof; these substituent pairs can also be joined into a carbocyclic or heterocyclic ring; preferred forms of R1 and R2 are the side chain substituents occurring in native polypeptides, oligonucleotides, variants or mimetics of these, carbohydrates, pharmacophores, variants or mimetics of these, or any other side chain substituent which can be attached to a scaffold or a backbone to produce a desired interaction with a target system; X represents an oxygen, sulfur, or nitrogen atom; and A and B are the substituents described above.

A chiral oxazolone derivative containing a blocked terminal amino group may be prepared from a blocked, disubstituted dipeptide, that was prepared by standard techniques known to those skilled in the art, as shown:

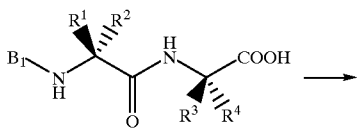

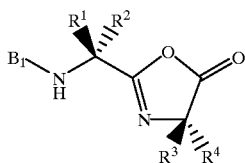

wherein $B_1$ is an appropriate protecting group, such as Boc. (t-butoxycarbonyl) or Fmoc (fluorenylmethoxycarbonyl). One may then use this oxazolone to acylate an amine, hydroxyl, or sulfhydryl-group in a linker structure or functionalized solid support, represented generically by AXH, using the reaction conditions described above. This acylation is followed by deblocking, using standard amine deprotection techniques compatible with the overall structure of the amide (i.e., the amine protecting group is orthogonal with respect to any other protecting or functional groups that may be present in the molecule), and the resulting amino group is used for reaction with a new bifunctional oxazolone, generating a growing chiral polymeric structure, as shown below:

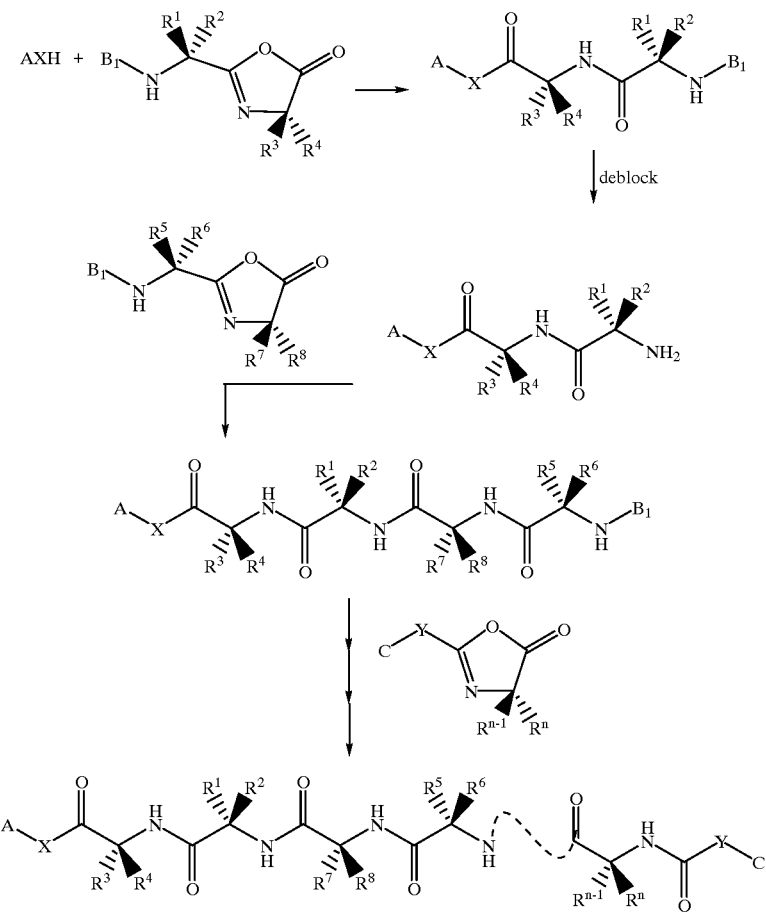

In the reaction shown above, Y is a linker (preferably a functionalized alkyl group); X is a nitrogen of suitable structure; an oxygen or a sulfur atom; each member of the substituent pairs $R^1$ and $R^2$, $R^3$ and $R^4$, $R^{n-1}$ and $R^n$ differs from the other and taken alone each signifies alkyl, cycloalkyl, or functionalized versions thereof; aryl, aralkyl or alkaryl or functionalized including heterocyclic versions thereof (preferably, these R substituents mimic the side-chain of naturally occurring amino acids); substituent R can also be part of a carbocyclic or heterocyclic ring; A is a substituent as described above; and C is a substituent selected from the set of structures for A; and $B_1$ is a blocking or protecting group.

Sub Assemblies

Alternatively, modular "sub assemblies" capable of conferring higher order structural properties may be pre-constructed and assembled together using these same reaction sequences in a manner which allows control of the higher order structure. This is illustrated for the case of a polymer formed with a repeating pattern of alternating modules of the type:

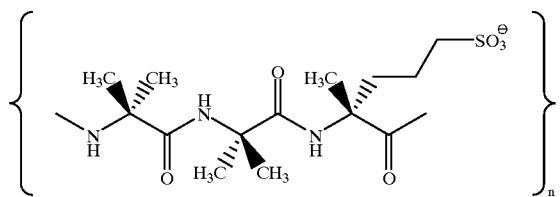

This polymer will form 3–10 helices, driven by the conformational restrictions imposed by the repetitive viscinal disubstitution. This triadic periodicity results in the formation of a helical superstructure which has charged sulfonate groups lined up regularly along one side of the helix:

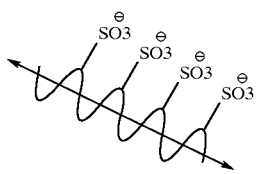

This "sub assembly" strategy may be used to generate higher order polymers in the following manner:

1. An oxazolone dimer containing a blocked terminal amino group may be prepared from a blocked disubstituted peptide, prepared using standard techniques known to those skilled in. the art, as shown:

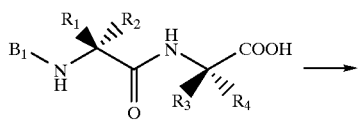

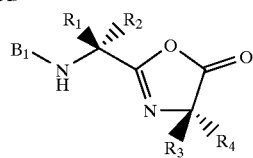

2. This oxazolone may be coupled with a suitable c-terminal derivative of a second disubstituted dipeptide, as shown, to give the 4-mer module shown:

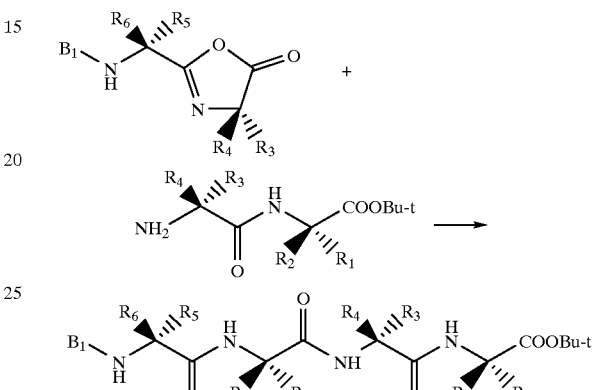

3. This process may then be repeated with the 4-mers to produce an 8-mer module; repeated again to form a 16-mer module, and so on, until a molecule having the desired length is obtained. At any point in this sequence, the protecting groups can be removed and the modules can be catenated together to form a polymer with repeating sequences of modules, as shown:

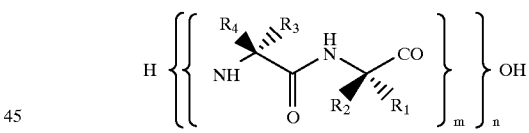

where m=number of iterative steps

In cases where solubility problems are encountered as the size of the modules increases, the stability of the linkages allows the use of a broad array of standard or "exotic" reaction solvents, such as hexamethyl phosphoramide. If necessary, solubilizing groups can be incorporated as side chain substituents or connecting modules.

Other Reactive Elements

At any point in the polymer syntheses shown above, a structural species, possessing (1) a terminal OH, —SH or —$NH_2$ group capable of ring-opening addition to the oxazolone and (2) another terminal group capable of reacting with the amino group of a chiral alpha, alpha'-disubstituted amino acid, may be inserted in the polymer backbone as shown below

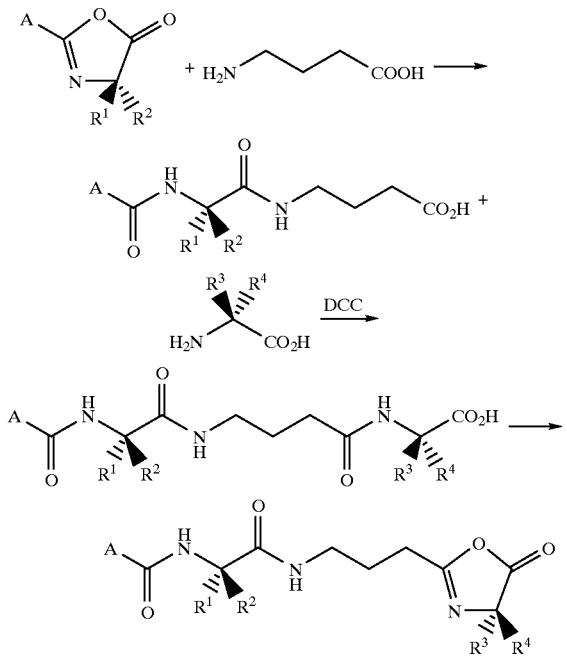

This process may be repeated, if desired, at each step in the synthesis where an oxazolone ring is produced. The bifunctional species used may be the same or different in the steps of the synthesis.

The experimental procedures described above for oxazolone formation and use of oxazolones as acylating agents are expected to be useful in the oxazolone-directed catenations. Solubility and coupling problems that may arise in specific cases can be dealt with effectively by one with ordinary skill in the art of polypeptide and peptide mimetic synthesis. For example, special solvents such as dipolar aprotic solvents (e.g., dimethyl formamide, DMF, dimethyl sulfoxide, DMSO, N-methyl pyrollidone, etc.) and chaotropic (molecular aggregatebreaking) agents (e.g., urea) will be very useful as catenations produce progressively larger molecules.

POLYMERS PRODUCED FROM AMINIMIDES

Stepwise sequential Reactions of 1,1-Disubstituted Hydrazines or Hydrazine Derivatives with Bifunctionally Reactive elements.

The aminimide monomer structure may be represented by the formula:

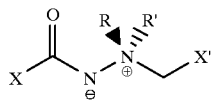

where R & R' are the same or different and X & X' are from the same groups as R or R:' and/or represent the extension or remainder of a polymer chain.

The groups R & R' may be of a subset of hydrophilic substituents such as, but not limited to hydroxymethyl, hydroxyethyl, hydroxypropyl, thioethyl, thiomethyl; carboxymethyl, carboxyethyl, ethylcarboxamido, methylcarboxamido; aminomethyl, aminoethyl, aminopropyl, guanindinylpropyl, guanidinylbutyl; mono-, di-, and triaminobenzyl, mono-, di-, and trinitrobenzyl; mono-, di-, tri-, and tetrahydroxy benzyl, mono- or polyhydroxyaryl (e.g. pyrogallol); heteroaryl (e.g. alkylpyridines, imidazole, alkyltryptophans); alkyl nucleotides; all substituted pyrimidylalkyl and substituted purinealkyl moieties; mono-, di-, and oligosaccharide (e.g. N-methylfucosamine, maltose and the calicheamicin recognition sequence respectively); alkylsulfonates, alkylphosphonates; a-polyfluoroketones; secondary, tertiary and quaternaryamines; hydrazines and the hydrazinium salts. They may also come from the subset consisting of hydrophobic substituents such as, but not limited to hydrogen; methyl, ethyl propyl, isopropyl, butyl, sec-butyl, isobutyl, tert-butyl, pentyl, iso-, sec-, and neopentyl, hexyl, heptyl, octyl, nonyl, decyl, etc.; vinyl, propenyl, butenyl or other alkenyl groups; acetylenic side chains; aromatic polycyclics (e.g. biphenyl, binaphthyl, naphthylphenyl, phenylnaphthyl); fused aromatic polycyclics (e.g. anthracene, phenylene, pyrene, acenaphthene, azulenes); fused polycyclics (e.g. decalin, hydrindanes, steroids); phenyl , alkylphenyl, phenylalkyl; benzyl, mono-, di-, tri-, and tetraalkylbenzyl; mono-, di-, and trialkoxybenzyl; heteroaryl (e.g. furyl, xanthanyl, quinolyl); methoxyalkyl, ethoxyalkyl, aryloxy; methylmercaptans, ethylmercaptans, alkyl thioethers and arylthioethers; dyes and fluorescent tags (such as rhodamine or fluorescein); alkyl esters, aryl esters, aralkyl esters, and alkylaryl esters; polymeric support surfaces.

Polymerization of Aminimide Subunits via Acylation/Alkylation Cycles

The following steps are involved in this synthesis:

1. Acylation of a hydrazinium salt with a molecule capable of functioning both as an acylating and as an alkylating agent producing an aminimide; BrCH2COCl and other bifunctional species, such as bromoalkyl isocyanates, 2-bromoalkyl oxazolones, etc., may be used as acylating agents under the reaction conditions given above.

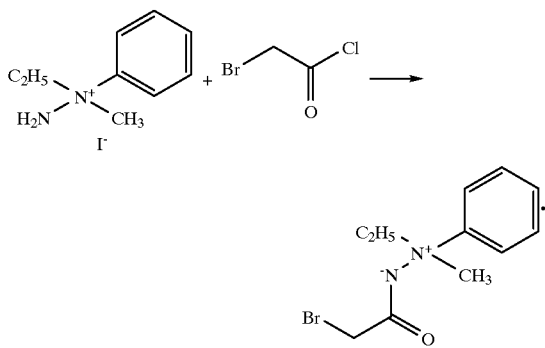

2. Reaction of the product of the above reaction with a 1,1-disubstituted hydrazine to form an aminimide hydrazinium salt.

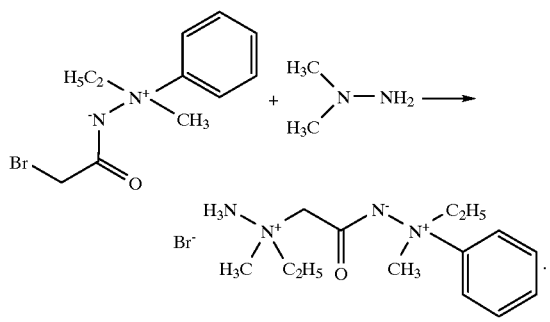

3 Acylation of the product from step 2 with a bifunctional acyl derivative similar to those listed in step 1 above producing a dimer.

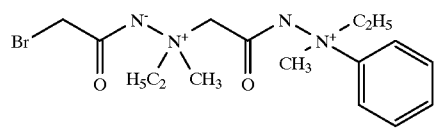

54 Repetition of steps 2 and 4 the required number of times to build the desired aminimide polymeric sequence.

6. Capping of the assembled sequence if desired, for example, by reaction with an acylating agent, such as acetyl chloride.

The experimental conditions (e.g. reaction-solvent, temperature and time, and purification procedures for products) for all of the above reactions were described above and are also well-known and practiced in the art. As the molecular weight of the products increases (e.g. in step 5 above) solubility and reaction-rate problems may develop if the reactions are run under the conditions that successfully gave products of much smaller molecular weight. As is well known from the art of peptide synthesis, this is probably due to conformational (folding) effects and to aggregation phenomena, and procedures found to work in the related peptide cases are expected to be very useful in the case of aminimide catenations. For example, reaction solvents such as DMF, or N-methyl pyrollidone, and chaotropic (aggregate-breaking) agents, such as urea, are expected to be helpful in alleviating reactivity problems as the molecular-weight of the product increases.

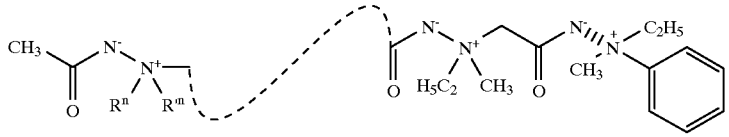

Polymerization of Aminimide Subunits via Acylation/Alkylation Cycles

The following steps are involved in this synthesis; e.

1. Alkylation of an asymmetrically disubstituted hydrazide, prepared as outlined above, with a molecule capable of functioning both as an alkylating and an acylating agent to form a racemic mixture of aminimides; as before the use of BrCH2COCl is shown below, but other bifunctional species, such as bromoalkyl isocyanates, 2-bromoalkyl oxazolones, etc. may also be used.

2. Reaction of the racemate from above with an asymmetrically disubstituted hydrazine to form the hydrazide:

3. Alkylation of the product from step 3 with a bifunctional molecule capable of alkylation and acylation, which may be the same as that used in step 1 or different, to form a mixture of diastereomeric aminimides.

4. Reaction of the product from step 4 with a suitable asymmetrically disubstituted hydrazine to form the hydrazide, as shown:

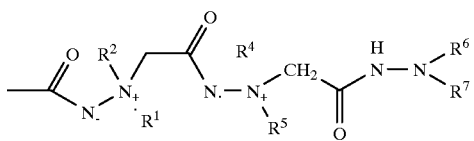

6. Repetition of steps 4, and 5 to build the desired aminimide polymer sequence.

8. Capping of the sequence, if desired, using e.g. methyl bromide to produce a sequence such as shown below.

Polymerization of Aminimide Subunits Using Hydrazinolysis of an Ester in the Presence of an Epoxide The following steps are involved in this synthesis:

1. Formation of an aminimine from the reaction of an 1,1-asymmetrically disubstituted hydrazine with an epoxide;:

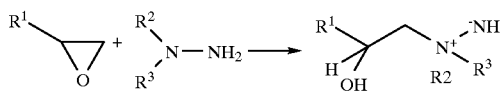

2. The aminimine is reacted with an ester-epoxide to give an aminimide;

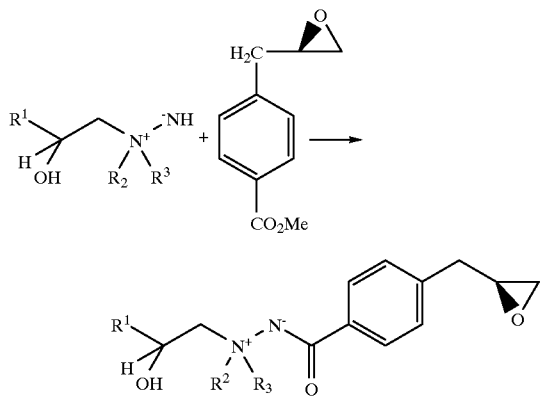

3. Reaction of the aminimide with an asymmetrically disubstituted hydrazine to form an aminimide-aminimine

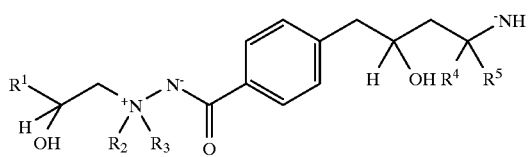

4. Repetition of steps 2 and 3 using the appropriate hydrazines and epoxy-esters in each step to produce the desired aminimide sequence.

5. "Capping" of the final sequence, if desired, by acylation with a simple ester, such as methyl acetate, to produce the designed aminimide ligand shown:

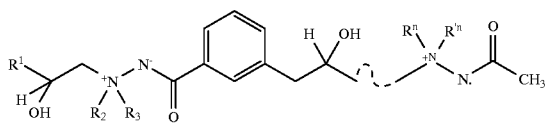

Synthesis of Hydrazides 1,1-disubstituted hydrazine with an activated acyl derivative or an isocyanate, in a suitable organic solvent, e.g. methylene chloride, toluene, ether, etc. in the presence of a base such as triethylamine to neutralize the haloacid generated during the acylation.

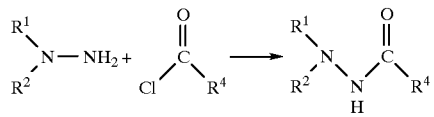

Activated acyl derivatives include acid chlorides, chlorocarbonates, chlorothiocarbonates, etc.; the acyl derivative may also be replaced with a suitable carboxylic acid and a condensing agent such as dicyclohexylcarbodiimide (DCC).

An example of the latter is the synthesis of the trifluoromethylhydrazides shown below:

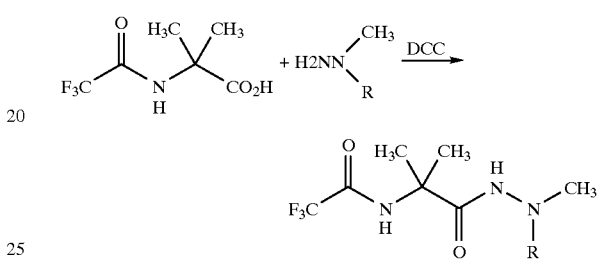

In this reaction a solution of 2-trifluoroacetamidoisobutyric acid in dry THF is stirred and an equivalent amount of dicyclohexylcarbodiimide is added. The reaction is subsequently strirred for three minutes, after which an equimolar quantity of the 1-substituted-1-methylhydrazine is added neat. Dicyclohexylurea precipitates immediately. The resultant suspension is stirred for one hour, filtered to remove the insoluble urea and the solvent is removed on a rotary evaporator to afford the crude hydrazide.

The desired 1,1-disubstituted hydrazines may be readily prepared in a number of ways well known in the art; one is the reaction of a secondary amine with NH2Cl in an inert organic solvent.

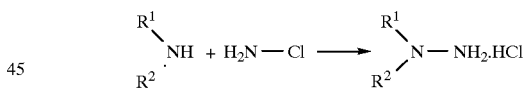

A second synthetic route for the preparation of hydrazines is alkylation of monoalkyl hydrazines, shown below for methyl hydrazine:

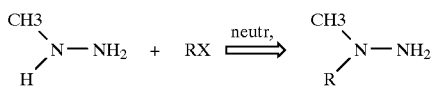

This reaction is carried out by reacting a solution of methylhydrazine in THF, cooled at 0° C. with a solution of an equimolar amount of the alkyl halide in THF added dropwise with stirring over a period of 30 minutes. The reaction is stirred at 0° C. for another 15 minutes, then heated to reflux and held at reflux for two hours. A water-cooled downward condenser is set up and approximately half of the solvent is removed by distillation. The residue is poured into water, which is then made basic by the addition of concentrated aqueous NaOH. The layers are separated, the aqueous phase is extracted with ether and the combined organic phases are washed with water, dried over MgSO₄ and concentrated by distillation. Distillation at reduced pressure affords the 1-substituted-1-methylhydrazine as a colorless liquid.

Polymers Produced by Hydrazides

Polymers containing designed sequences of substituted hydrazones may be produced using the following steps:

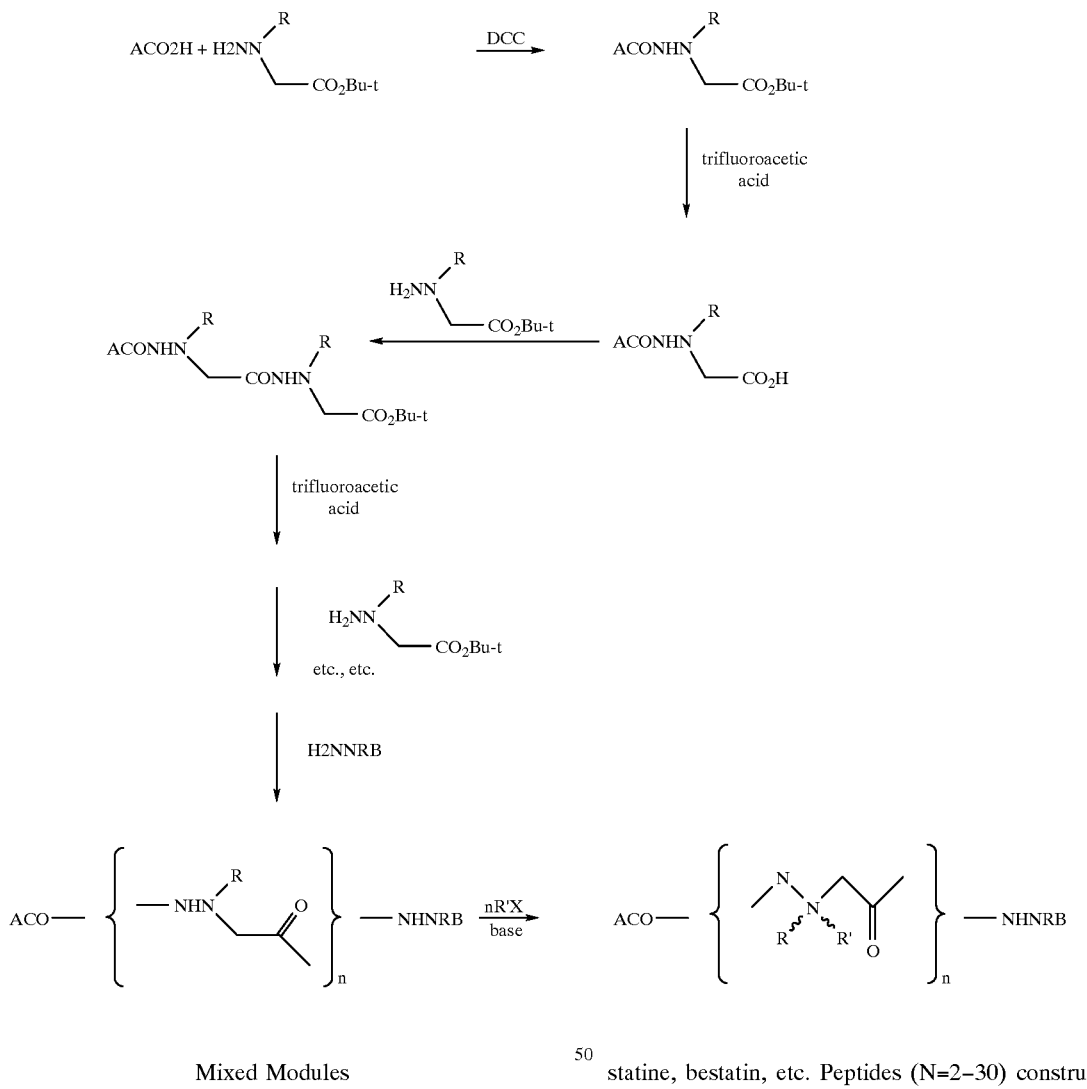

Mixed Modules

All of the oxazolone, aminimide and hydrazide modules and monomers illustrated above may be mixed and matched to provide a variety of mixed-backbone polymers having specific properties, functionalities and sequences.

Substituents

Any of the various R and R' groups illustrated in all of the oxazolone, aminimide and hydrazide structures may be selected from among the following list:

1) Amino acid derivatives of the form (AA)N, which would include, for example, natural and synthetic amino acid residues (N=1) including all of the naturally occuring alpha amino acids, especially alanine, arginine, asparagnine, aspartic acid, cysteine, glutamine, glutamic acid, glycine, histidine, isoleucine, leucine, lysine, methionine, phenylalanine, proline, serine, threonine, tryptophan, tyrosine; the naturally occuring disubstituted amino acids, such as amino isobutyric acid, and isovaline, etc.; a variety of synthetic amino acid residues, including alpha-disubstituted variants, species with olefinic substitution at the alpha position, species having derivatives, variants or mimetics of the naturally occuring side chains; N-Substituted glycine residues; natural and synthetic species known to functionally mimic amino acid residues, such as statine, bestatin, etc. Peptides (N=2–30) constructed from the amino acids listed above, such as angiotensinogen and its family of physiologically important angiotensin hydrolysis products, as well as derivatives, variants and mimetics made from various combinations and permutations of all the natural and synthetic residues listed above. Polypeptides (N=31–70), such as big endothelin, pancreastatin, human growth hormone releasing factor and human pancreatic polypeptide. Proteins (N>70) including structural proteins such as collagen, functional proteins such as hemoglobin, regulatory proteins such as the dopamine and thrombin receptors.

2) Nucleotide derivatives of the form (NUCL)N, which includes natural and synthetic nucleotides (N=1) such as adenosine, thymine, guanidine, uridine, cystosine, derivatives of these and a variety of variants and mimetics of the purine ring, the sugar ring, the phosphate linkage and combinations of some or all of these. Nucleotide probes (N=2–25) and oligonucleotides (N>25) including all of the various possible homo and heterosynthetic combinations and permutations of the naturally occuring nucleotides, derivatives and variants containing synthetic purine or pyrimidine species or mimics of these, various sugar ring mimetics, and a wide variety of alternate backbone analogues including but not limited to phosphodiester, phosphorothionate, phosphorodithionate, phosphoramidate, alkyl phosphotriester, sulfamate, 3'-thioformacetal, methylene(methylimino), 3-N-carbamate, morpholino carbamate and peptide nucleic acid analogues.

3) Carbohydrate derivatives of the form (CH)n. This would include natural physiologically active carbohydrates such as including related compounds such as glucose, galactose, sialic acids, beta-D-glucosylamine and nojorimycin which are both inhibitors of glucosidase, pseudo sugars, such as 5a-carba-2-D-galactopyranose, which is known to inhibit the growth of Klebsiella pneumonia (n=1), synthetic carbohydrate residues and derivatives of these (n=1) and all of the complex oligomeric permutations of these as found in nature, including high mannose oligosaccharides, the known antibiotic streptomycin (n>1).

4) A naturally occurring or synthetic organic structural motif. This term is defined as meaning an organic molecule having a specific structure that has biological activity, such as having a complementary structure to an enzyme, for instance. This term includes any of the well known base structures of pharmaceutical compounds including pharmacophores or metabolites thereof. These include beta-lactams, such as pennicillin, known to inhibit bacterial cell wall biosynthesis; dibenzazepines, known to bind to CNS receptors, used as antidepressants; polyketide macrolides, known to bind to bacterial ribosymes, etc. These structural motifs are generally known to have specific desirable binding properties to ligand acceptors.

5) A reporter element such as a natural or synthetic dye or a residue capable of photographic amplification which possesses reactive groups which may be synthetically incorporated into the oxazolone structure or reaction scheme and may be attached through the groups without adversely interfering with the reporting functionality of the group. Preferred reactive groups are amino, thio, hydroxy, carboxylic acid, carboxylic acid ester, particularly methyl ester, acid chloride, isocyanate alkyl halides, aryl halides and oxirane groups.

6) An organic moiety containing a polymerizable group such as a double bond or other functionalities capable of undergoing condensation polymerization or copolymerization. Suitable groups include vinyl groups, oxirane groups, carboxylic acids, acid chlorides, esters, amides, lactones and lactams. Other organic moiety such as those defined for R and R' may also be used.

7) A macromolecular component, such as a macromolecular surface or structures which may be attached to the oxazolone modules via the various reactive groups outlined above in a manner where the binding of the attached species to a ligand-receptor molecule is not adversely affected and the interactive activity of the attached functionality is determined or limited by the macromolecule. This includes porous and non-porous inorganic macromolecular components, such as, for example, silica, alumina, zirconia, titania and the like, as commonly used for various applications, such as normal and reverse phase chromatographic separations, water purification, pigments for paints, etc.; porous and non-porous organic macromolecular components, including synthetic components such as styrene-divinyl benzene beads, various methacrylate beads, PVA beads, and the like, commonly used for protein purification, water softening and a variety of other applications, natural components such as native and functionalized celluloses, such as, for example, agarose and chitin, sheet and hollow fiber membranes made from nylon, polyether sulfone or any of the materials mentioned above. The molecular weight of these macromolecules may range from about 1000 Daltons to as high as possible. They may take the form of nanoparticles (dp=100–1000 Angstroms), latex particles (dp=1000–5000 Angstroms), porous or non-porous beads (dp=0.5–1000 microns), membranes, gels, macroscopic surfaces or functionalized or coated versions or composites of these.

8) A structural moiety selected from the group including cyano, nitro, halogen, oxygen, hydroxy, alkoxy, thio, straight or branched chain alkyl, carbocyclic aryl and substituted or heterocyclic derivatives thereof, wherein R and R' may be different in adjacent n units and have a selected stereochemical arrangement about the carbon atom to which they are attached;

As used herein, the phrase linear chain or branched chained alkyl groups means any substituted or unsubstituted acyclic carbon-containing compounds, including alkanes, alkenes and alkynes. Alkyl groups having up to 30 carbon atoms are preferred. Examples of alkyl groups include lower alkyl, for example, methyl, ethyl, n-propyl, iso-propyl, n-butyl, iso-butyl or tert-butyl; upper alkyl, for example, cotyl, nonyl, decyl, and the like; lower alkylene, for example, ethylene, propylene, propyldiene, butylene, butyldiene; upper alkenyl such as 1-decene, 1-nonene, 2,6-dimethyl-5-octenyl, 6-ethyl-5-octenyl or heptenyl, and the like; alkynyl such as 1-ethynyl, 2-butynyl, 1-pentynyl and the like. The ordinary skilled artisan is familiar with numerous linear and branched alkyl groups, which are within the scope of the present invention.

In addition, such alkyl group may also contain various substituents in which one or more hydrogen atoms has been replaced by a functional group. Functional groups include but are not limited to hydroxyl, amino, carboxyl, amide, ester, ether, and halogen (fluorine, chlorine, bromine and iodine), to mention but a few. Specific substituted alkyl groups can be, for example, alkoxy such as methoxy, ethoxy, butoxy, pentoxy and the like, polyhydroxy such as 1,2-dihydroxypropyl, 1,4-dihydroxy-1-butyl, and the like; methylamino, ethylamino, dimethylamino, diethylamino, triethylamino, cyclopentylamino, benzylamino, dibenzylamino, and the like; propanoic, butanoic or pentanoic acid groups, and the like; formamido, acetamido, butanamido, and the like, methoxycarbonyl, ethoxycarbonyl or the like, chloroformyl, bromoformyl, 1,1-chloroethyl, bromoethyl, and the like, or dimethyl or diethyl ether groups or the like.

As used herein, substituted and unsubstituted carbocyclic groups of up to about 20 carbon atoms means cyclic carbon-containing compounds, including but not limited to cyclopentyl, cyclohexyl, cycloheptyl, admantyl, and the like. Such cyclic groups may also contain various substituents in which one or more hydrogen atoms has been replaced by a functional group. Such functional groups include those described above, and lower alkyl groups as described above. The cyclic groups of the invention may further comprise a heteroatom. For example, in a specific embodiment, $R_2$ is cycohexanol.

As used herein, substituted and unsubstituted aryl groups means a hydrocarbon ring bearing a system of conjugated double bonds, usually comprising an even number of 6 or more (pi) electrons. Examples of aryl groups include, but are not limited to, phenyl, naphthyl, anisyl, toluyl, xylenyl and the like. According to the present invention, aryl also includes aryloxy, aralkyl, aralkyloxy and heteroaryl groups, e.g., pyrimidine, morpholine, piperazine, piperidine, benzoic acid, toluene or thiophene and the like. These aryl groups may also be substituted with any number of a variety of functional groups. In addition to the functional groups described above in connection with substituted alkyl groups and carbocylic groups, functional groups on the aryl groups can be nitro groups.

As mentioned above, these structural moieties can also be any combination of alkyl, carbocyclic or aryl groups, for example, 1-cyclohexylpropyl, benzylcyclohexylmethyl, 2-cyclohexyl-propyl, 2,2-methylcyclohexylpropyl, 2,2-methylphenylpropyl, 2,2-methylphenylbutyl, and the like.

Reactive Groups

Specifically preferred reactive groups to generate the aminimide and oxazolone structures and the resulting base modules are listed below in tables 1, 2 and 3. The bonds in the structures in these figures represent potential points of attachment to the first and second compounds and to the base modules.

Specifically preferred reactive groups to generate the aminimide and oxazolone structures and the resulting base modules are listed below in tables 1, 2 and 3. The bonds in the structures in these figures represent potential points of attachment for the attachment of the structural diversity elements to the first and second compounds and to the base modules.

TABLE 1

Oxazolone Modules

| Reactivity Groups | | Base Modules |
|---|---|---|
| [structure] | HY—<br>(Y = N,S,O) | [structure] |
| [structure] | $\underset{/}{\overset{\backslash}{>}}C=O$ | [structure] |
| [structure] | HY—<br>(Y = N,S,O) | [structure] |
| $\underset{H_2}{N}\!\!\!\diagdown\!\!\!\diagup\!\!\!CO_2H$ | —CO2H/Cl<br>(ClCO2Et/Et3N) | [structure] |
| [structure] | HX—<br>( X=S—,N<br>( Z=CH2=CH—, etc.) | [structure] |

—Represents potential points of attachment

TABLE 2

Aminimide Modules

| Reactivity Groups | | Base Modules |
|---|---|---|
| —COOH | H2NN\< | —CONHN\< |
| —NCO | H2NN\< | —NHCONHN\< |
| —OCOCl | H2NN\< | —OCONHN\< |
| —SCOCl | H2NN\< | —SCONHN\< |
| —CONHN\< | —X (neutr.) | —CONN⊖\|⊕— |
| —CONHN\< | <epoxide> | —CONN⊖\|⊕—CH2CH(OH)CH3 |
| —NHCONHN\< | —X (neutr.) | —NHCONN⊖\|⊕— |
| —NHCONHN\< | <epoxide> | —NHCONN⊖\|⊕—CH2CH(OH)CH3 |
| —OCONHN\< | —X (neutr.) | —OCONN⊖\|⊕— |
| —OCONHN\< | <epoxide> | —OCONN⊖\|⊕—CH2CH(OH)CH3 |
| —SCONHN\< | —X (neutr.) | —SCONN⊖\|⊕— |

TABLE 2-continued

Aminimide Modules

| Reactivity Groups | | Base Modules |
|---|---|---|
| —SCONHN(/\) | (epoxide) | —SCONN⊖⊕(/\)OH |
| H2NN(/\) | —X (neutr.) | H2NN⊕— X⊖ |
| H2NN(/\) | (epoxide) | HNN⊖⊕(/\)OH |
| H2NN⊕— X⊖ | BASE | HNN⊖⊕— |
| HNN⊖⊕— | —COOR | —CONN⊖⊕— |
| HNN⊖⊕—CH2—CH(OH)—CH3 | —COOR | —CONN⊖⊕—CH2—CH(OH)—CH3 |
| HNN⊖⊕— | (dimethylsuccinic anhydride) | (dimethylsuccinic acid amide with N⊕(CH3)3, CO2H) |
| HNN⊖⊕—CH2—CH(OH)—CH3 | (dimethylsuccinic anhydride) | (dimethylsuccinic acid amide with N⊕—N⊖—CH2—CH(OH)—CH3, CO2H) |

—Represents potential points of attachment

TABLE 3

Aminimide-Oxazolone Modules

| Reactivity Groups | | Base Modules |
|---|---|---|
| HNN⊖⊕—CH2—CH(OH)—CH3 | (dimethyl oxazolone) | (urea-linked product with OH) |

TABLE 3-continued

Aminimide-Oxazolone Modules

| Reactivity Groups | | Base Modules |
|---|---|---|
| H2NN—<br>⊖ \|⊕<br>X<br>(Base) | (oxazolone structure) | (base module structure) |

—Represents potential points of attachment

EXAMPLE 1

This example describes preparation of a tetramer by alternating ring-opening/Michael-addition reactions followed by chain polymerizations.

Step 1

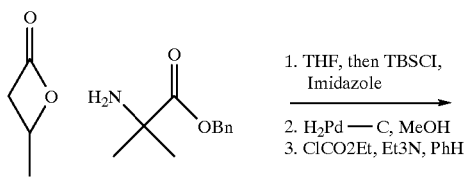

In the first synthetic step, a solution of b-butyrolactone (8.61 g, 0.1 mole, 8.15 mL) in THF (150 mL) is cooled at 0° C. while a solution of benzyl 2-aminoisobutyrate (19.3 g, 0.1 mole) in THF (100 mL) is added. The mixture is stirred at 0° C. for two hours, then room temperature for four hours, then is treated with tert-butyldimethylsilyl chloride (15.1 g, 0.1 mole) and imidazole (13.6 g, 0.2 mole) added in alternating portions as the solids. The mixture is stirred overnight at room temperature, the solids are removed by filtration, and the filtrate is concentrated in vacuo. The residue is dissolved in methanol (100 mL), palladium on carbon catalyst (5% Pd, 500 mg) is added, and the solution stirred under an atmosphere of hydrogen gas until the ester is exhausted (reaction is monitored in progress by volume of absorbed $H_2$ gas and by TLC). Following complete removal of the benzyllic functionality, the catalyst is removed by filtration with the aid of celite. The precipitate is washed with methanol (3×100 mL) and the combined filtrates are concentrated in vacuo. The residue is crystallized, then recrystallized from ethyl acetate to afford the protected acid (21.7 g, 0.072 mole, 72%).

This acid is dissolved in ethyl acetate (300 mL) and cooled at 0° C. while ethyl chloroformate (7.77 g, 0.072 mole, 6.85 mL) is added, followed by triethylamine (7.25 g, 0.072 mole, 9.98 mL). After cessation of gas evolution (ca. four hours), the triethylamine hydrochloride is removed by filtration and the filtrate is concentrate to afford crude 2-(2-tert-butyldimethylsilyloxy propyl)-4,4-dimethyl-5-oxazolone as a yellow oil (23.4 g). Recrystallization from ethyl acetate affords the pure product (13.7 g, 67%, 0.048 mole). The material gave satisfactory spectral data (300 MHz NMR proton signals corresponding to silyl group butyl:silyl group methyls:oxazolone gem-dimethyl integrals 9:6:6; IR 1820 $cm^{-1}$ azlactone band).

Step 2

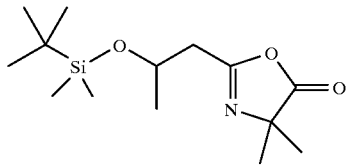

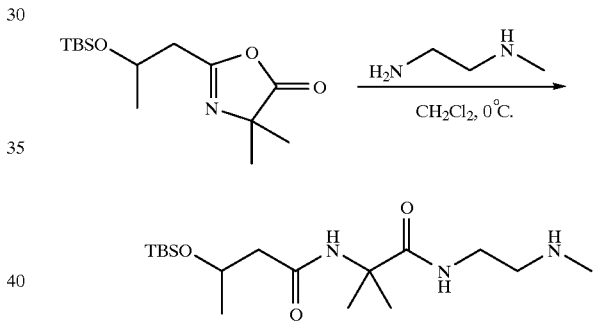

A solution of of 95% N-methylethylenediamine (3.56 g, 48 mmol, 4.23 mL) in methylene chloride (75 mL) is cooled in an ice bath while a solution of 2-(2-tert-butyldimethylsilyloxy propyl)-4,4-dimethyl-5-oxazolone (13.7 g, 48 mmol) in methylene chloride (100 mL) is added such that the temperature remains below 5° C. The solution is stirred at room temperature for 15 minutes while a white precipitate forms. The mixture is stirred for an additional 2 h at 0° C. The solids are removed by filtration and washed with methylene chloride (25 mL) and air dried to yield the ring-opened adduct (12.87 g, 36 mmol, 75%), identified by nuclear magnetic resonance (NMR) and Fourier transform infrared (FTIR) spectroscopy as follows: NMR ($CDCl_3$) :$CH_3$-N/gem $(CH_3)_2$ ratio 1:2; tert-butyldimethylsilyl— splitting pattern in 0–1 ppm region, integration ratios and $D_2O$ exchange experiments diagnostic for structure. FTIR (nujol mull): azlactone CO band at 1820 $cm^{-1}$ absent; strong amide bands present in 1670–1700 $cm^{-1}$ region.

Step 3

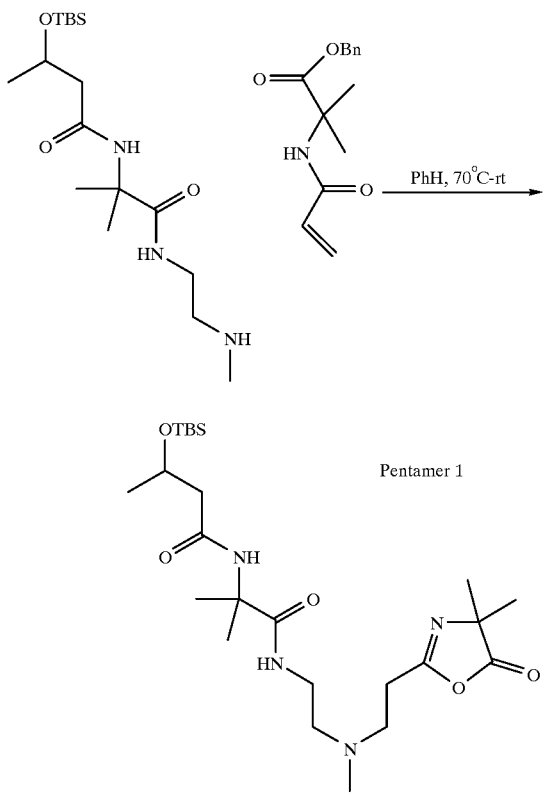

Pentamer 1

A solution of of the ring-opened adduct (8.98 g, 25 mmol) and 4,4-dimethyl-2-vinylazlactone (3.48 g, 25 mmol) in benzene (50 mL) is heated to 70° C. for 4 hours. The flask is cooled to room temperature and allowed to stand under an inert atmosphere for 3 days. The solvent is decanted off from the thick oil that forms. This oil is dissolved in acetone (ca 50 mL) and concentrated to produce another thick oil, which is concentrated under vacuum at 1 torr overnight to yield 9.34 g of a white crystalline solid (25 mmol), identified by NMR and FTIR spectroscopy as 2-(N-(2-(2-(3-tert-butyldimethylsilyloxy butyramido)-isobutyramido)-ethyl)-N-methyl-2-aminoethyl)-4,4-dimethyl-5-oxazolone: NMR: $CH_3$-N/gem $(CH_3)_2$ ratio 1:4; tert-butyldimethylsilyl— splitting pattern in 0–1 ppm region, integration ratios and $D_2O$ exchange experiments diagnostic for structure. FTIR (nujol mull): strong azlactone CO band at 1820 cm$^{-1}$.

Construction of the Poly(pentamer)

25 mL, 25 mmol) is added. The exotherm is controlled by the rate of addition of the fluoride reagent. The mixture is then heated briefly to 70° C. and cooled to room temperature. Water 100 mL) is added and the layers are stirred, then separated. The organic phase is dried (sat'd aq NaCl, $MgSO_4$), and concentrated in vacuo (18 torr, then 0.1 torr 10 hours) to afford the polymer (9.60 g). This material showed no signals for the tert-butyldimethylsilyl group in the proton NMR spectrum and the azlactone band was absent in the infrared spectrum.

EXAMPLE 2

This example illustrates the preparation of a tris (pentameric) module and its assembly into a polymer.

Step 1

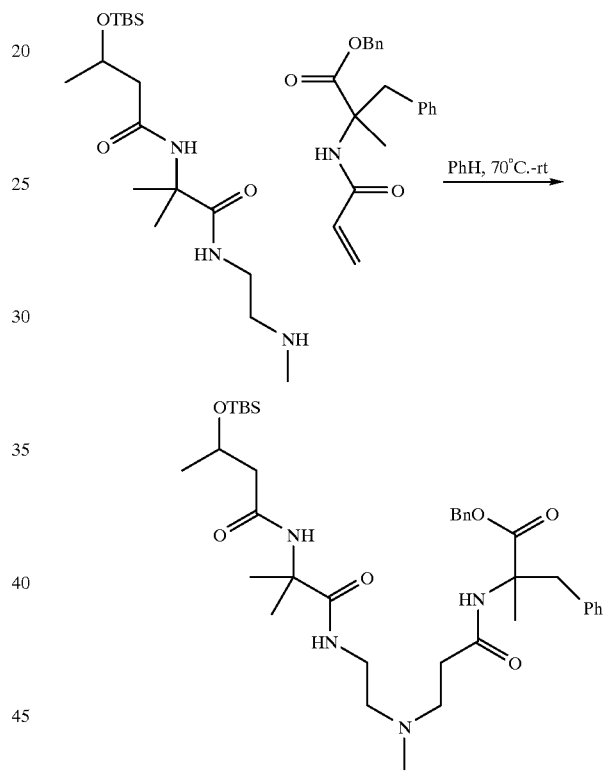

A solution of of the ring-opened adduct (8.98 g, 25 mmol) and benzyl 3-phenyl-2-methyl-2-acrylamidopropionate (8.03 g, 25 mmol) in benzene (50 mL) is heated to 70° C. for 4 hours. The flask is cooled to room temperature and allowed to stand under an inert atmosphere for 3 days. The solvent

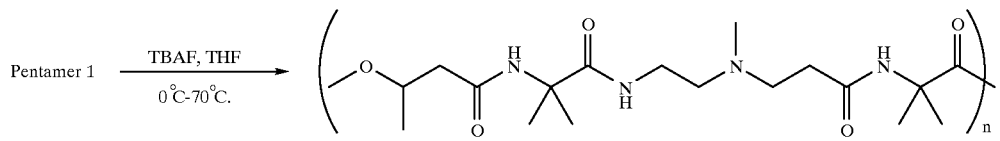

Polymerization of the mono(pentamer)—This material is dissolved in THF (500 mL) and cooled at 0° C. while a solution of tetra-n-butylammonium fluoride (1.0M in THF, is decanted off from the thick oil that forms. The residue is crystallized, then recrystallized from ethyl acetate, to afford the protected benzyl ester adduct (15.34 g, 23 mmol, 90%)

Step 2

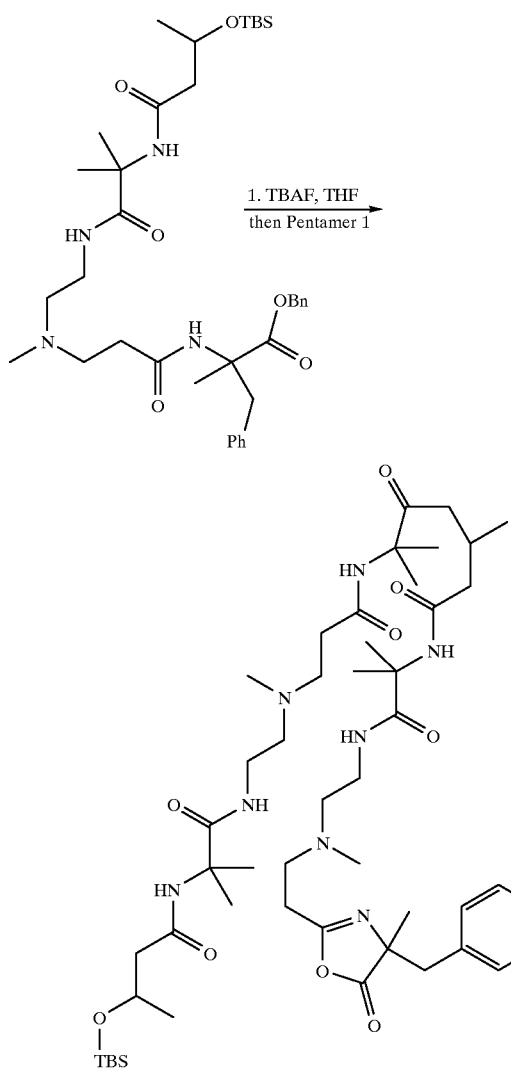

1. TBAF, THF then Pentamer 1

The product is dissolved in THF (250 mL) and a solution of TBAF (1.0 M, 23 mmol, 23 mL) is added and the reaction stirred for one hour at room temperature, then cooled at 0° C. while a solution of 2-(N-(2-(2-(3-tert-butyldimethylsilyloxy. butyramido)-isobutyramido)-ethyl)-N-methyl-2-aminoethyl)-4,4-dimethyl-5-oxazolone (11.45 g, 23 mmol) in THF (150 mL) is added with stirring. The reaction is stirred overnight at room temperature, then partitioned between water (200 mL) and THF. The aqueous phase is separated and extracted with ether (2×200 mL) and the combined organics are dried (sat'd aq NaCl, MgSO$_4$) and concentrated to afford a solid (22.0 g).

A suspension of this solid and palladium on carbon catalyst (5% Pd, 500 mg) in methanol (200 mL) is stirred under an atmosphere of hydrogen gas until the ester is exhausted (reaction is monitored in progress by volume of absorbed H$_2$ gas and by TLC). Following complete removal of the benzylic functionality, the catalyst is removed by filtration with the aid of celite. The filter pad is washed with methanol (3×100 mL) and the combined filtrates are concentrated in vacuo to afford a viscous syrup that is used directly.

This acid is dissolved in ethyl acetate (100 mL) and cooled at 0° C. while ethyl chloroformate (2.32 g, 23 mmol, 2.04 mL) is added, followed by triethylamine (2.16 g, 23 mmol, 2.98 mL). After cessation of gas evolution (approximately two hours), the triethylamine hydrochloride is removed by filtration and the filtrate is concentrated to afford the crude product as a yellow oil (23.4 g). A pure sample of this product is obtained Purified by chromatographic purification on RP-C$_{18}$ silica gel (methanol-water gradient elution) to give 2-(N-(2-(3-(2-(N-(2-(2-(3-tert-butyldimethyl silyloxybutyramido)-isobutyramido)-ethyl)-N-methyl-3-propanamido)-isobutyroxy)-butyramido)-isobutyramido)-ethyl-N-methyl-2-aminoethyl)-ethyl-4,4-dimethyl-5-oxazolone (11.43 g, 61%, 14 mmol) as an amorphous powder. The material gave satisfactory spectral data (300 MHz NMR proton signals corresponding to silyl group butyl:silyl group methyls:oxazolone gem-dimethyl integrals 9:6:6; IR 1820 cm$^{-1}$ azlactone band).

Step 3

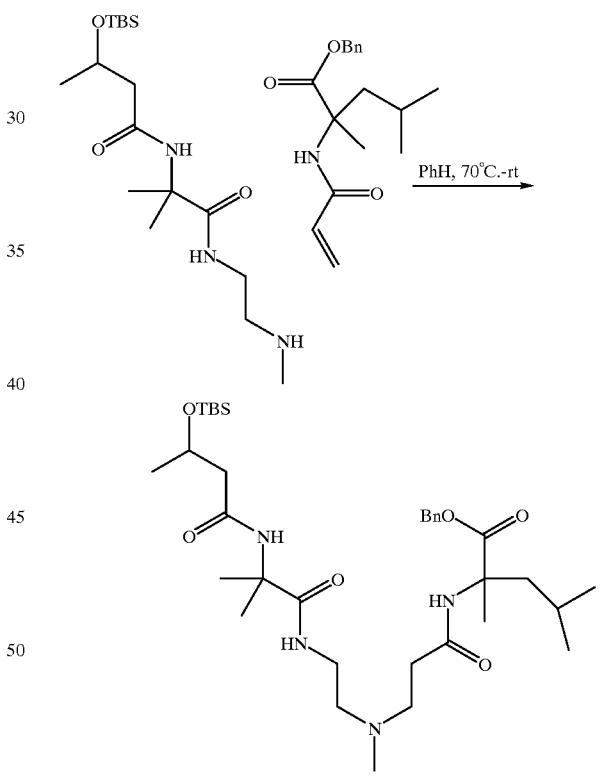

PhH, 70°C.-rt

A solution of of the ring-opened adduct (8.98 g, 25 mmol) and benzyl 2,4-dimethyl-2-acrylamidopentanoate (7.18 g, 25 mmol) in benzene (50 mL) is heated to 70° C. for 4 hours. The flask is cooled to room temperature and allowed to stand under an inert atmosphere for 3 days. The solvent is decanted off from the thick oil that forms. The residue is crystallized, then recrystallized from ethyl acetate to afford the protected benzyl ester adduct (13.41 g, 21 mmol, 83%)

Step 4

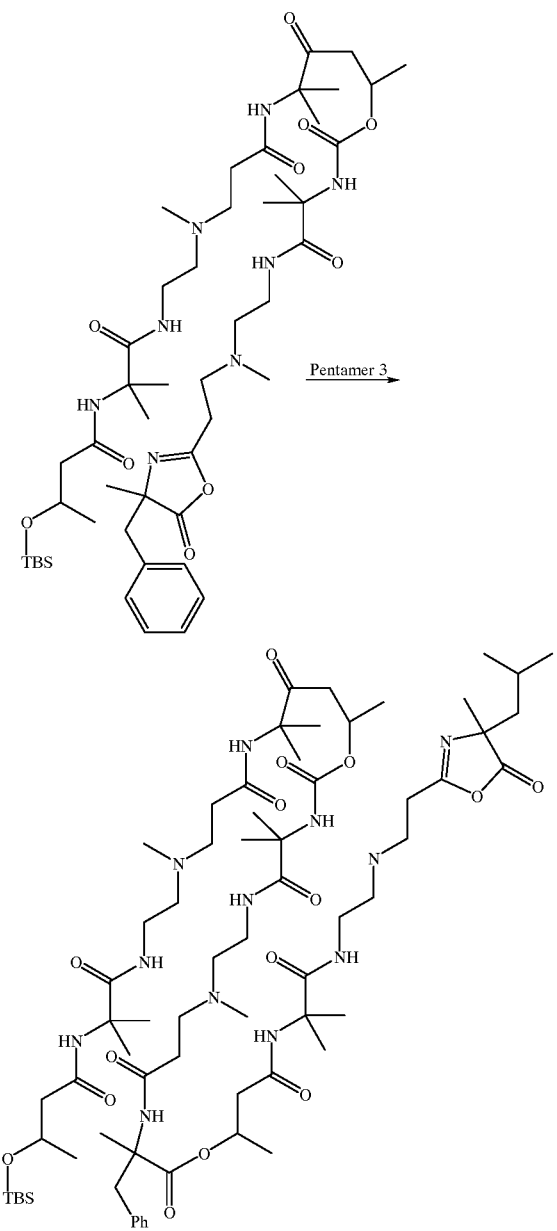

A solution of this product (8.94 g, 14 mmol) in THF (250 mL) and a solution of TBAF (1.0 M, 14 mmol, 14 mL) is added and the reaction stirred for one hour at room temperature, then cooled at 0° C. while a solution of the previously prepared di-pentamer oxazolone (11.43 g, 14 mmol) in THF (150 mL) is added with stirring. The reaction is stirred overnight at room temperature, then partitioned between water (200 mL) and THF. The aqueous phase is separated and extracted with ether (2×200 mL) and the combined organics are dried (sat'd aq NaCl, $MgSO_4$) and concentrated to afford a solid (22.0 g).

A suspension of this solid and palladium on carbon catalyst (5% Pd, 250 mg) in methanol (200 mL) is stirred under an atmosphere of hydrogen gas until the ester is exhausted (reaction is monitored in progress by volume of absorbed $H_2$ gas and by TLC). Following complete removal of the benzylic functionality, the catalyst is removed by filtration with the aid of celite. The filter pad is washed with methanol (3×100 mL) and the combined filtrates are concentrated in vacuo to afford a viscous syrup that is used directly.

This acid is dissolved in ethyl acetate (100 mL) and cooled at 0° C. while ethyl chloroformate (1.41 g, 14 mmol, 1.24 mL) is added, followed by triethylamine (1.31 g, 14 mmol, 1.81 mL). After ten hours, the triethylamine hydrochloride is removed by filtration and the filtrate is concentrated to afford the crude product as a tan solid (23.4 g). Purification by column chromatography on RP-$C_{18}$ silica gel (methanol-water gradient elution), pooling of the appropriate fractions and concentration in vacuo affords pure 2-(3-(N-(2-(2-(2-(3-(N-(2-(3-(2-(N-(2-(2-(3-tert-butyldimethylsilyloxybutyramido)-isobutyramido)-ethyl)-N-methyl-2-aminoethyl)-propanoylamido)-isobutyroxy)-butyramido)-isobutyramido)-ethyl)-N-methyl-2-aminoethyl)-propanoylamido)-isobutyroxy)-propanoylamido)-isobutyramido)-N-methyl-ethylamino)-ethyl)-4-isobutyl-4-methyl-5-oxazolone z(3.72 g, 22%, 3 mmol) as an amorphous powder. The material gave satisfactory spectral data (300 MHz NMR proton signals corresponding to silyl group butyl:silyl group methyls:oxazolone gem-dimethyl integrals 9:6:6; IR 1820 $cm^{-1}$ azlactone band).

Construction of the Polytris(pentamer)

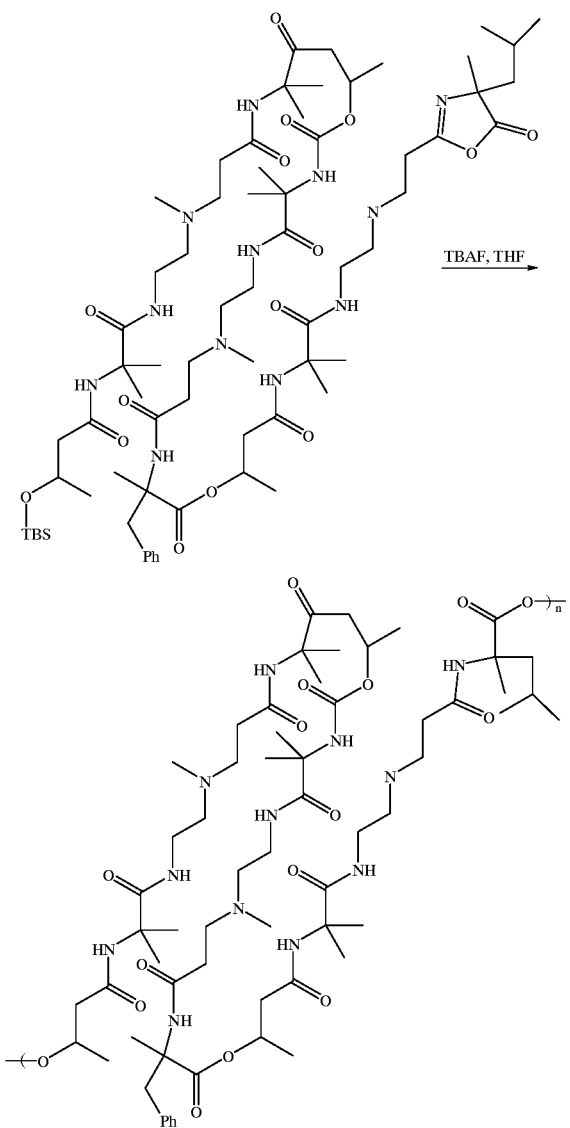

Polymerization of the tris(pentamer)—This material is dissolved in THF (200 mL) and cooled at 0° C. while a solution of tetra-n-butylammonium fluoride (1.0 M in THF, 3 mL, 3 mmol) is added. The exotherm is controlled by the rate of addition of the fluoride reagent. The mixture is then heated briefly to 70° C. and cooled to room temperature. Water (100 mL) is added and the layers are stirred, then separated. The organic phase is dried (sat'd aq NaCl, MgSO$_4$), and concentrated in vacuo (18 torr, then 0.1 torr 10 hours) to afford the polymer (3.38 g). This material showed no signals for the tert-butyldimethylsilyl group in the proton NMR spectrum and the azlactone band was absent in the infrared spectrum.

Further details on the reaction possibilities for the oxazolone and aminimide compounds can be found in two PCT applications PCT/US93/0—and PCT/US93/0—, each filed on Dec. 28, 1993, and entitled Modular Design And Synthesis Of Oxazolone-Derived Molecules and Modular Design And synthesis Of Aminimide-Derived Molecules, respectively. The content of each of those applications is expressely incorporated herein by reference thereto to the extent necessary to understand the metes and bounds of this invention.

What is claimed is:

1. A method of making a polymer having specific physiochemical properties which comprises:

forming modules having a structure which includes at least one orthogonal reactivity element for reaction with another module and two structural diversity elements which impart a desired physical property to a polymer which is made from joining together at least two modules; and reacting the reactivity element of a first module with the reactivity element of a second module by a stepwise addition reaction to effect a controlled polymerization, whereby the modules are joined together to form a polymer having specific physiochemical properties and the reacting step is carried to completion before any additional reacting steps are undertaken to join additional modules to the polymer.

2. A method according to claim 1 which further comprises forming the base module from an aminimide compound, an oxazolone compound or derivatives thereof.

3. A method according to claim 1 which further comprises forming the base module by reacting a first compound having at least one structural diversity element and a first reactive group, with a second compound having at least one structural diversity element and a second reactive group, wherein the first and second groups combine by an addition reaction.

4. The method according to claim 3 which further comprises producing the first compound by forming an oxazolone compound having at least one structural diversity element attached thereto.

5. The method according to claim 4 which further comprises providing the second compound as a nucleophile or carbonyl compound which is capable of reaction with the oxazolone and which contains at least one structural diversity element.

6. The method according to claim 5 which further comprises combining the first and second compounds to form a base module having one of the following structures:

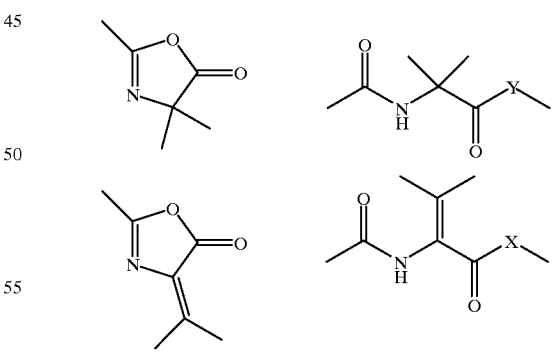

wherein at least two of the unconnected lines are connected to structural diversity elements.

7. The method according to claim 3 which further comprises providing at least one of the first and second compounds with at least two structural diversity elements.

8. The method according to claim 1 which further comprises providing each of the first and second compounds with at least two structural diversity elements.

9. A method according to claim 1 which further comprises sequentially reacting at least three modules to form the polymer.

10. A method according to claim 1 which further comprises reacting a plurality of the same modules to form the polymer.

11. A method according to claim 1 which further comprises reacting a plurality of different modules to form the polymer.

12. A method according to claim 1 which further comprises selecting the module to be a derivative or mimic of a peptide, protein, oligonucleotide, oligosaccharide, carbohydrate, pharmaceutical or pharmacophore.

13. A method of making a polymer having specific physiochemical properties including a particular water solubility which comprises:

forming a first module having at least one orthogonal reactivity element for reaction with another module, at least two structural diversity elements, and at least one hydrophobic moiety;

forming a second module having at least one orthogonal reactivity element for reaction with another module, at least two structural diversity elements, and at least one hydrophilic moiety; and joining together the first and second modules by reacting the reactivity element of the first module with the reactivity element of the second module by a stepwise addition reaction to effect a controlled polymerization, whereby the modules are joined together to form a polymer having specific physiochemical properties including a specific molecular weight, a specific length and a particular water solubility.

14. A method according to claim 13 which further comprises sequentially reacting at least one additional module to form the polymer.

15. A polymer comprising at least three connected modules wherein the modules are connected by an addition reaction, and at least one module has a structure which includes at least two structural diversity elements.

16. A polymer according to claim 15 wherein each module has a structure which includes at least two structural diversity elements.

17. A polymer according to claim 15 wherein the first and last modules have less than two structural diversity elements.

18. A polymer made according to the method of claim 1.

19. A polymer made according to the method of claim 7.

20. A polymer made according to the method of claim 13.

21. A method of making a polymer having specific physiochemical properties including a particular water solubility which comprises:

forming a first module having a hydrophobic moiety attached thereto, at least one orthogonal reactivity element for reaction with another module and one or more points of attachment for structural diversity elements;

forming a second module having a hydrophilic moiety attached thereto, at least one orthogonal reactivity element for reaction with another module and one or more points of attachment for structural diversity elements; and joining together the first and second modules by reacting the reactivity element of the first module with the reactivity element of the second module by a stepwise addition reaction to control the addition of each module to a developing polymer chain to form a polymer having specific physiochemical properties including a specific molecular weight, a specific length and a particular water solubility.

22. The method of claim 21, wherein the reacting step is carried to completion before any additional reacting steps are undertaken to join additional modules to the polymer.

23. A polymer made according to the method of claim 21.

24. The method of claim 13, wherein the reacting step is carried to completion before any additional reacting steps are undertaken to join additional modules to the polymer.

* * * * *